(12) United States Patent
Zicker et al.

(10) Patent No.: US 11,077,165 B2
(45) Date of Patent: Aug. 3, 2021

(54) USE OF ANTIOXIDANTS FOR GENE MODULATION

(75) Inventors: Steven Curtis Zicker, Lawrence, KS (US); Inke Paetau-Robinson, Auburn, KS (US); Karen Joy Wedekind, Meriden, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 1133 days.

(21) Appl. No.: 11/718,963

(22) PCT Filed: Nov. 9, 2005

(86) PCT No.: PCT/US2005/040515
§ 371 (c)(1),
(2), (4) Date: Jun. 5, 2007

(87) PCT Pub. No.: WO2006/053010
PCT Pub. Date: May 18, 2006

(65) Prior Publication Data
US 2008/0069834 A1 Mar. 20, 2008

Related U.S. Application Data

(60) Provisional application No. 60/626,162, filed on Nov. 9, 2004.

(51) Int. Cl.
| | |
|---|---|
| A61K 36/00 | (2006.01) |
| A61K 38/06 | (2006.01) |
| A23K 20/174 | (2016.01) |
| A23K 20/142 | (2016.01) |
| A23K 20/121 | (2016.01) |
| A23K 50/40 | (2016.01) |
| A61K 31/085 | (2006.01) |
| A61K 31/355 | (2006.01) |

(52) U.S. Cl.
CPC .......... *A61K 38/063* (2013.01); *A23K 20/121* (2016.05); *A23K 20/142* (2016.05); *A23K 20/174* (2016.05); *A23K 50/40* (2016.05); *A61K 31/085* (2013.01); *A61K 31/355* (2013.01)

(58) Field of Classification Search
None
See application file for complete search history.

(56) References Cited

U.S. PATENT DOCUMENTS

| | | | |
|---|---|---|---|
| 5,621,117 A | 4/1997 | Bethge et al. | |
| 5,668,117 A * | 9/1997 | Shapiro | A61K 31/195 436/518 |
| 6,090,414 A | 7/2000 | Passwater | |
| 6,136,859 A | 10/2000 | Henriksen | |
| 6,184,227 B1 | 2/2001 | Karmali | |
| 6,352,712 B1 * | 3/2002 | Lukaczer | A61K 36/53 424/439 |
| 6,465,466 B1 * | 10/2002 | Bergman | A61K 31/495 514/250 |
| 6,596,762 B2 | 7/2003 | Sokol | |
| 6,858,399 B2 * | 2/2005 | Lamb | G01N 33/5005 435/2 |
| 6,974,841 B1 * | 12/2005 | Rapisarda | 514/783 |
| 7,709,460 B2 * | 5/2010 | McCaddon | 514/52 |
| 2001/0043983 A1 | 11/2001 | Hamilton | |
| 2002/0012715 A1 * | 1/2002 | Soldati | A61K 8/673 424/766 |
| 2002/0077349 A1 * | 6/2002 | Hamilton | 514/440 |
| 2002/0119182 A1 * | 8/2002 | Zicker | A23K 20/142 424/442 |
| 2002/0182196 A1 * | 12/2002 | McCleary | A61K 31/00 424/94.1 |
| 2002/0183382 A1 | 12/2002 | Sokol | |
| 2003/0036203 A1 * | 2/2003 | Duke | G01N 33/5091 436/71 |
| 2003/0091518 A1 * | 5/2003 | Pauly | A61P 17/16 424/59 |
| 2003/0100601 A1 * | 5/2003 | Schmitz | A23G 1/30 514/453 |
| 2003/0161863 A1 * | 8/2003 | Ballevre | A61P 29/00 424/439 |
| 2003/0198661 A1 * | 10/2003 | Harper | A61K 31/015 424/442 |
| 2004/0097404 A1 * | 5/2004 | Kessler | A23L 33/175 514/43 |
| 2004/0220242 A1 * | 11/2004 | Shapiro | A61K 31/00 514/364 |

(Continued)

FOREIGN PATENT DOCUMENTS

| | | |
|---|---|---|
| AU | 2004238375 | 11/2004 |
| GB | 2 367 489 A | 4/2002 |

(Continued)

OTHER PUBLICATIONS

Asensi et al. (Ratio of Reduced to Oxidized Glutathione as Indicator or Oxidative Stress Status and DNA Damage, Methods in Enzymology, vol. 299 pp. 267-276 (1999)) (Year: 1999).*
Morel et al. (The Journal of Biological Chemistry, 273:26969 (1998)) (Year: 1998).*
Robertson et al. ("Nonalcoholic Steatosis and Steatohepatitis II. Cytochrome P-450 enzymes and oxidative stress", Am J Physiol Gastrointest Liver Physiol 281: G1135-G1139, 2001) (Year: 2001).*
Mihalick et al. ("Folate and Vitamin E deficiency Impair Cognitive Performance in Mice Subjected to Oxidative Stress" Neuromolecular Medicine vol. 4, 2003 pp. 197-201) (Year: 2003).*
D. P. Jones, "Redox Potential of GSH/GSSG Couple: Assay and Biological Significance", *Methods in Enzymology*, vol. 348, pp. 93-112, (2002).

(Continued)

*Primary Examiner* — Michael Barker
*Assistant Examiner* — Randall O Winston

(57) ABSTRACT

The invention provides (1) methods for modulating gene expression in senescent mammals by administering antioxidant-comprising compositions to the mammals and (2) antioxidant-comprising compositions that modulate gene expression and/or reduce the oxidative stress of such mammals.

19 Claims, 5 Drawing Sheets

(56) References Cited

U.S. PATENT DOCUMENTS

| | | | |
|---|---|---|---|
| 2005/0027004 A1* | 2/2005 | Kyle | A61K 31/20 514/560 |
| 2005/0106170 A1* | 5/2005 | Cheung | A61K 36/06 424/195.16 |
| 2005/0226942 A1* | 10/2005 | Myhill | A61K 36/16 424/725 |
| 2005/0244422 A1* | 11/2005 | Mascarenhas | A61K 38/10 424/185.1 |
| 2005/0249788 A1* | 11/2005 | Reynolds | A61K 31/12 424/442 |
| 2005/0266051 A1 | 12/2005 | Kelley | |
| 2006/0057185 A1* | 3/2006 | Akimoto | A61K 31/202 424/439 |
| 2006/0094734 A1* | 5/2006 | Newman | 514/263.31 |
| 2007/0036870 A1* | 2/2007 | Bryan | A21D 2/02 424/642 |
| 2008/0057039 A1* | 3/2008 | Rogers et al. | 424/93.7 |
| 2008/0069834 A1 | 3/2008 | Zicker et al. | |

FOREIGN PATENT DOCUMENTS

| | | | |
|---|---|---|---|
| JP | 58129954 A * | 8/1983 | |
| WO | WO9833495 A1 * | 8/1998 | |
| WO | WO 00/44375 | 8/2000 | |
| WO | WO0057876 A1 * | 10/2000 | |
| WO | WO 01/17366 | 3/2001 | |
| WO | WO0138395 A1 * | 5/2001 | |
| WO | 02/35943 A | 5/2002 | |
| WO | WO 02/71874 | 1/2003 | |
| WO | 03/013268 A | 2/2003 | |
| WO | WO03033662 A2 * | 4/2003 | |
| WO | WO 02/45525 | 5/2003 | |
| WO | WO003075677 A1 * | 9/2003 | |
| WO | 2005/006877 A | 1/2005 | |

OTHER PUBLICATIONS

T. Takeda, "Senescence-Accelerated Mouse (SAM): A Novel Murine Model of Senescence", *Experimental Gerontology*, vol. 32, Nos. 1/2, pp. 105-109, (1997).

T. Takeda, "Pathobiology of the Senescence-Accelerated Mouse (SAM)", *Experimental Gerontology*, vol. 32, pp. 117-127, (1997).

T. Takeda, "Senescence-Accelerated Mouse (SAM): A Biogerontological Resource in Aging Research", *Neurobiology of Aging*, vol. 20, pp. 105-110, (1999).

European Search Report 05 85 1449.

Ames et al., 1998, "The Free Radical Theory of Aging Matures," Physiol. Rev. 78(2):547-581.

Bloom et al, 2003, "Phosphorylation of Nrf2 at Ser40 by protein kinase C in response to antioxidants leads to the release of Nrf2 from INrf2, but is not required for Nrf2 stabilization/accumulation in the nucleus and transcriptional activation of antioxidant response element-mediated NAD(P)H:quinone oxidoreductase-I gene epression," J. Biol. Chem. 278(45):44675-4682.

Brigelius-Flohe et al., 1999, "Vitamin E: Function and Metabolism," FASEB J. 13(10):1145-1155.

Crayhon, 2002, "The Real Power of Antioxidants," Total health 20(2):27-35.

Dezhong, "Study of Vitamin E Against Liver Fibrosis," Chongqing Medical Journal 29:79-80.

Fang, 2000, "Vitamin E, Vitamin C, and Gene Stability," Foreign Medical Sciences (Section Hygiene) 29(3):141-144.

Frei, 1999, "Molecular and Biological Mechanisms of Antioxidant Action," FASEB J. 13(9):963-964.

Gradelet et al., 1996, "Effects of canthaxanthin, astaxanthin, lycopene and lutein on liver xenobiotic-metabolizing enzymes in the rat," Xenobiotica 26(1):49-63.

Harman, 1993, "Free Radical Theory of Aging: A Hypothesis on Pathogenesis of Senile Dementia of the Alzheimer's Type," Age 16(1):23-30.

International Search Report and Written Opinion in International Application. No. PCT/US05/040515 dated May 26, 2006.

Lovell et al., 1997, "Elevated 4-Hydroxynonenal in Ventricular Fluid in Alzheimer's Disease," Neurobiology of Aging 18(5):457-461.

Ma et al., 2003, "Inhibition of nuclear factor kappaB by phenolic antioxidants: interplay between antioxidant signaling and inflammatory cytokine expression," Molecular Pharmacology 64(2):211-219.

Markesbery et al., 1998, "Four-hydroxynonenal, a product of lipid peroxidation, is increased in the brain in Alzheimer's disease," Neurobiology of Aging 19(1):33-36.

Michaud et al., 2002, "Proteomic Approaches for the Global Analysis of Proteins," Biotechniques 33(6):1308-1316.

Oxidant Sensitive Signal Transduction and Gene Expression, 1999, http://www.thaiwave.com/networkantioxidants/geneexpression.htm.

Rayment et al., 2003, "Vitamin C supplementation in normal subjects reduces constitutive ICAM-1 expression," Biochem. Biophys. Res. Commun. 308(2)339-345.

Xiaodong et al., 1999, "Effect f VE + VC on Malonaldehyde (MDA) and Cell Cycle in Liver of Aged Mice," J.N. Bethune Univ. Med. Sci., 25(5):606-607.

Yanping et al., 2002, "Nutrition and Health of Vegetable and Fruit," Food and Nutrition in China 2002(2):43-45.

Kumaran et al., "L-Carnitine and DL-a-lipoic acid reverse the age-related deficit in glutathione redox state in skeletal muscle and heart tissues," Mechanisms of Ageing and Development, 2004, 125:507-512.

Milgram et al., 2002, "Dietary enrichment counteracts age-associated cognitive dysfunction in canines," Neurobiology of Aging 23:737-745.

Milgram et al., 2004, "Long-term treatment with antioxidants and a program of behavioral enrichment reduces age-dependent impairment in discrimination and reversal learning in beagle dogs," Experimental Gerontology 39:753-765.

* cited by examiner

USE OF ANTIOXIDANTS FOR GENE MODULATION

CROSS REFERENCE TO RELATED APPLICATIONS

This application claims priority to U.S. Provisional Application Ser. No. 60/626,162, filed Nov. 9, 2004, the disclosure of which is incorporated herein by this reference.

FIELD OF TEE INVENTION

This invention is directed generally to methods of modulating gene expression in senescent mammals, and more particularly to methods of modulating gene expression in senescent mammals by administering antioxidant-comprising compositions. This invention also is directed generally to antioxidant-comprising compositions that modulate gene expression in senescent mammals and/or reduce the oxidative stress of those mammals.

BACKGROUND OF THE INVENTION

Living cells continuously produce free radicals during their normal functions. Free radicals are highly reactive substances capable of reacting irreversibly with many biological molecules, thus causing progressive deterioration of the biological system. Free radicals are normally neutralized by the body's production of antioxidant enzymes and nutrient-derived antioxidants. Free radical-induced oxidative stress is a major factor in the long-term tissue degradation associated with aging.

Although much is known about antioxidants and their function in mammals, there continues to be a need for alternative antioxidant-comprising compositions and knowledge about the effect of those compositions on mammals, and particularly on senescent mammals.

SUMMARY OF THE INVENTION

The invention provides methods for modulating gene expression in senescent mammals. The methods comprise administering to the mammal an antioxidant-comprising composition (i.e., a composition comprising one or more antioxidants, and optionally additional ingredients). The total amount of the one or more antioxidants in the composition is sufficient to effect modulation of expression of one or more genes in one or more tissues in the senescent mammal.

In various embodiments, the senescent mammal is a non-human mammal, a companion animal, a canine, or a feline.

In some embodiments, each of the one or more genes whose expression is modulated is independently a cytochrome P450 family gene, an apolipoprotein family gene, a gene encoding one or more products that regulate hemodynamic properties, a heat shock protein family gene, a gene encoding one or more products indicative of DNA damage, a gene encoding one or more products that regulate cell cycle, a pro-inflammatory gene, a gene encoding one or more proteins associated with a chromaffin secretory pathway, a gene encoding one or more products that regulate gene transcription, an NF-KB pathway gene, a gene encoding one or more products related to immune function, a gene encoding one or more glycolytic enzymes, a gene encoding one or more mitochondrial oxidative pathway proteins, or a gene encoding one or more ribosomal proteins.

In various embodiments, one or more of the genes whose expression is modulated comprise a cytochrome P450 family gene; an apolipoprotein family gene; a gene encoding one or more products that regulate hemodynamic properties; a heat shock protein family gene; a gene encoding one or more products indicative of DNA damage; a gene encoding one or more products that regulate cell cycle; a pro-inflammatory gene; a gene encoding one or more proteins associated with a chromaffin secretory pathway; a gene encoding one or more products that regulate gene transcription; an NF-KB pathway gene; a gene encoding one or more products related to immune function; a gene encoding one or more glycolytic enzymes; a gene encoding one or more mitochondrial oxidative pathway proteins; or a gene encoding one or more ribosomal proteins.

In some embodiments, modulation of expression of one or more genes is effected in one or more of the adrenal gland, liver, or cerebral cortex.

In some embodiments, the antioxidant-comprising composition is fed to the senescent mammal.

In some embodiments, the composition comprises vitamin E, vitamin C, or both.

In some embodiments, the composition comprises one or more antioxidants selected from vitamin E, vitamin C, lipoic acid, astaxanthin, beta-carotene, L-carnitine, coenzyme Q10, glutathione, lutein, lycopene, selenium, N-acetylcysteine, soy isoflavone(s), S-adenosylmethionine, taurine, tocotrienol(s), and mixtures thereof.

In some embodiments, the composition comprises one or more antioxidants selected from spinach pomace, tomato pomace, citrus pulp, grape pomace, carrot granules, broccoli, green tea, corn gluten meal, rice bran, algae, curcumin, selenium, and mixtures thereof.

In some embodiments, the composition comprises one or more antioxidants selected from carrot granules, broccoli, green tea, corn gluten meal, rice bran, algae, curcumin, selenium, and mixtures thereof.

In some embodiments, the composition comprises one or more antioxidants selected from vitamin E, vitamin C, fruit(s), vegetable(s), carotenoids(s), flavonoid(s), polyphenol(s), and mixtures thereof.

This invention also is directed, in part, to antioxidant-comprising compositions that modulate gene expression in senescent mammals and to compositions that reduce the oxidative stress of senescent mammals.

Other and further objects, features, and advantages of the present invention will be readily apparent to those skilled in the art.

DETAILED DESCRIPTION OF THE INVENTION

Figure 1:
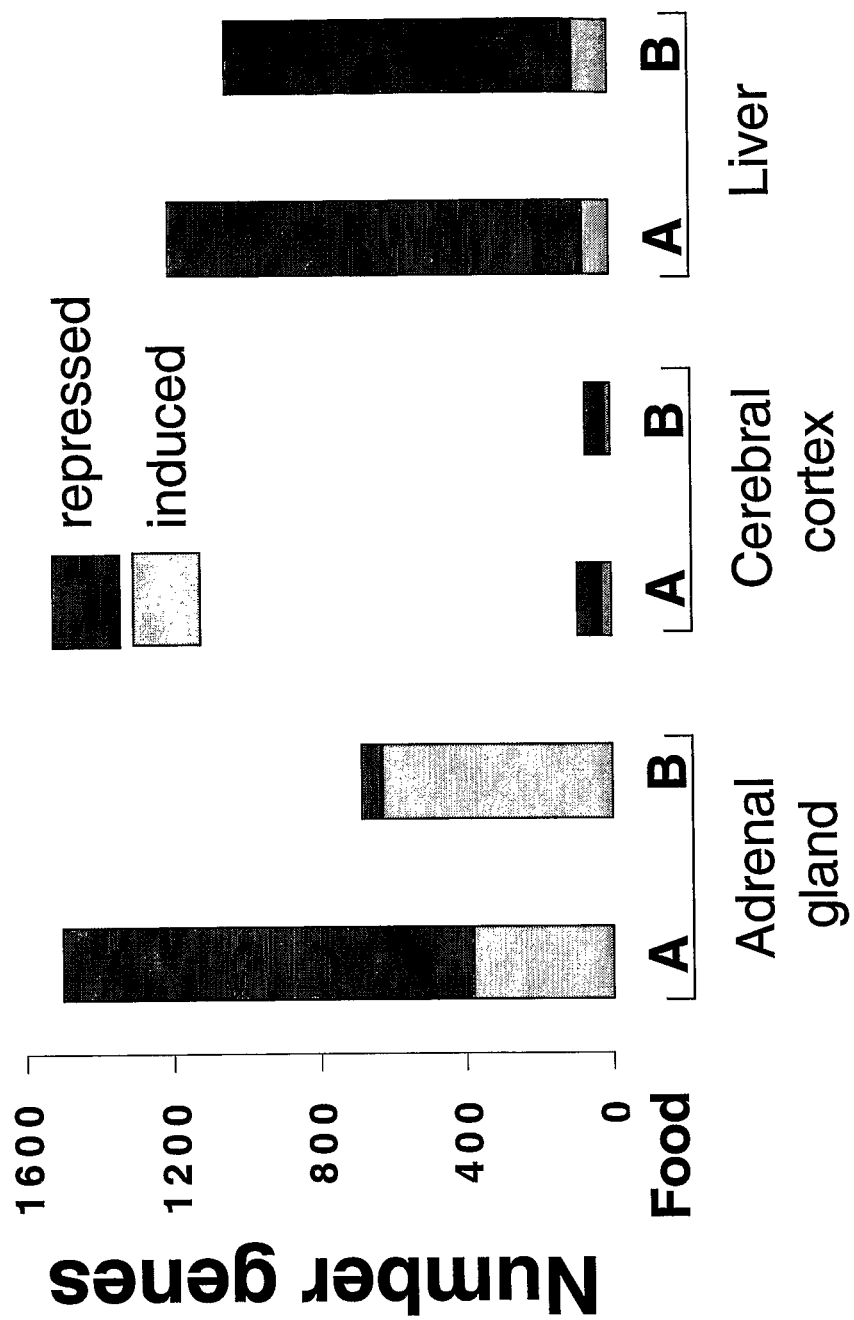
FIG. 1 shows tissue-specific modulation of gene expression in mice fed foods A and B.

This detailed description is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples are intended for purposes of illustration only. This invention, therefore, is not limited to the embodiments described in this specification, and may be variously modified.

In various embodiments, the present invention provides methods of modulating gene expression in a senescent mammal. The methods comprise administering to the senescent mammal an antioxidant-comprising composition (i.e., a composition comprising one or more antioxidants, and optionally additional ingredients). The total amount of the one or more antioxidants in the composition is sufficient to effect modulation of expression of one or more genes in the senescent mammal.

It is contemplated that the methods and compositions of the present invention may be useful for a variety of senescent mammals.

In various embodiments of this invention the mammal is a non-human mammal. For example, the non-human mammal can be a companion mammal (e.g., canine, feline), a primate mammal (e.g., monkey, baboon), a ruminant mammal (e.g., cow, sheep, goat, horse), or a rodent mammal (e.g., mouse, rat, guinea pig).

In various embodiments, the non-human mammal is a companion animal, a canine or a feline.

As used herein, a "senescent" mammal refers to a mammal that is aged. For example, a senescent canine is a canine that is at least seven years old; and a senescent feline is a feline that is at least seven years old.

The methods of this invention contemplate administration of a variety of antioxidant-comprising compositions to the mammal. Contemplated compositions include, for example, foods, supplements, treats, and toys (typically chewable and consumable toys). The antioxidant-comprising composition can be fed to the mammal as a component of its food intake. The food intake of the mammal can meet its ordinary nutritional requirements, which a skilled artisan can determine based upon the mammal's species, age, sex, weight, and other factors. For example, a typical food intake for a canine of 1-6 years of age, contains about 23% protein (% of dry matter), about 15% fat (% of dry matter), about 0.6% phosphorous (% of dry matter), and about 0.3% sodium (% of dry matter); and typical food intakes for older canines and felines (% of dry matter) are provided in Table 1.

TABLE 1

Food Intake for Older Canines and Felines

| Component | Canine | Feline |
|---|---|---|
| crude protein | 15-23 | 30-45 |
| crude fat | 7-15 | 10-25 |
| crude fiber | >2 | <10 |
| calcium | 0.5-1.0 | 0.6-1.0 |
| phosphorous | 0.25-0.75 | 0.5-0.7 |
| sodium | 0.15-0.35 | 0.2-0.5 |
| magnesium |  | 0.05-0.1 |
| energy density (kcal of ME/kg of food (dry matter)) | 3.0-4.0 | 3.5-4.5 |

In various embodiments, methods for modulating expression of one or more genes comprises administering to the mammal one or more antioxidants, including a combination or mixture of antioxidants. An antioxidant is any material that either directly quenches a free radical or indirectly causes a free radical to become quenched. One skilled in the art knows that a variety of materials have free radical quenching or absorbing capacity. For example, the following are raw ingredients that are high in oxygen radical absorbing capacity ("ORAC") content: spinach pomace, tomato pomace, citrus pulp, grape pomace, carrot granules, broccoli, green tea, *Ginkgo biloba*, corn gluten meal, algae, curcumin, astaxanthin, beta-carotene, carrot, glutathione, green tea, lutein, lycopene, N-acetylcysteine, polyphenols, soy isoflavones, spinach, S-adenosylmethionine, sulfur-containing amino acids, taurine, tocotrienols, vitamin C, and vitamin E. For example, when spinach pomace, tomato pomace, citrus pulp, grape pomace, and carrot granules were added to a composition as 1% inclusions (for a total of 5% substitution for a low ORAC ingredient such as corn), they increased both the ORAC content of the overall composition and the ORAC content of the plasma of the animals that ate that composition.

In many embodiments, an antioxidant can be, for example, astaxanthin (3,3'-dihydroxy-4,4',-diketo-beta-carotene), beta-carotene, coenzyme Q10 (ubiquinone), glutathione, L-carnitine, lipoic acid, lutein, lycopene, N-acetylcysteine, a polyphenol such as a flavonoid, S-adenosylmethionine, selenium, soy isoflavone, taurine, tocotrienol, vitamin C, or vitamin E.

In other embodiments, an antioxidant can be a food or a food product, for example, spinach (for example, spinach pomace), tomato (for example, tomato pomace), citrus fruit (for example, citrus pulp), grape (for example, grape pomace), carrot (for example, carrot granules), broccoli, green tea, *Ginkgo biloba*, corn gluten meal, rice bran, algae, curcumin, marine oil, or yeast (for example, selenium yeast), or mixtures thereof.

In other embodiments, an antioxidant can be a raw ingredient, for example, raw spinach pomace, raw tomato pomace, raw citrus pulp, raw grape pomace, raw carrot granules, raw broccoli, raw green tea, raw *Ginkgo biloba*, raw corn gluten meal, raw rice bran, or mixtures thereof.

In some embodiments, the antioxidant-comprising composition can comprise vitamin E, vitamin C, or both vitamin E and vitamin C.

In other embodiments, the antioxidant-comprising composition can comprise one or more antioxidants selected from vitamin E, vitamin C, L-carnitine, and lipoic acid.

In some embodiments, vitamin E can be administered as a tocopherol, a mixture of tocopherols, and/or various derivatives thereof, such as an ester derivative, for example, acetate, succinate, or palmitate ester of vitamin E. Vitamin E, as used herein, includes forms and derivatives that provide vitamin E-like activity after ingestion by the mammal. Vitamin E can be in alpha, beta, gamma, or delta configurations. Furthermore, vitamin E can be in either its d-stereoisomer configuration or as a racemic mixture.

Vitamin C can be administered to the mammal as ascorbic acid or various derivatives thereof, for example calcium phosphate salt of ascorbic acid, cholesteryl salt of ascorbic acid, or ascorbate-2-monophosphate. Vitamin C or a derivative thereof can be in any physical form, for example, a liquid, a semisolid, a solid or a heat stable form.

Lipoic acid can be alpha-lipoic acid or a lipoate salt or ester, for example, an isomer of lipoic acid described in U.S. Pat. No. 5,621,117. As used herein, "alpha-lipoic acid" is synonymous with "lipoic acid." Lipoic acid can be administered in various forms, for example, racemic mixture, salt(s), ester(s), and/or amide(s).

L-carnitine can be in a derivative form, for example, a salt (for example, hydrochloride), an ester (for example, fumarate ester or succinate ester), or as acetylated L-carnitine.

In some embodiments, an antioxidant or mixture of antioxidants can be fed to a mammal as a component of its food or as a food supplement. The quantities administered in the food, all as wt % (dry matter basis) of the food, are calculated as the active material, per se, that is measured as free material. The maximum antioxidant amount should not bring about toxicity. Preferably, the antioxidant, or mixture thereof, is fed to the mammal in amounts that are effective to modulate one or more genes in the mammal to which it is fed. The amounts will vary depending on the species of the mammal and the type of antioxidant(s).

In some embodiments, the vitamin E content of a composition is from at least about 250 ppm, at least about 500 ppm, or at least about 1,000 ppm. Although not necessary, a maximum of about 2,000 ppm, or of about 1,500 ppm is generally not exceeded.

In some embodiments, the vitamin C content of a composition is from at least about 50 ppm, at least about 75 ppm, or at least about 100 ppm, up to about 1,000 ppm, up to about 5,000 ppm, or up to about 10,000 ppm.

In some embodiments, the lipoic acid content of a composition is at least about 25 ppm, at least about 50 ppm, or at least about 100 ppm, up to about 100 ppm, or up to about 600 ppm, or up to an amount which is not toxic to the mammal.

In other embodiments, the range of lipoic acid content can be from about 100 ppm to about 200 ppm.

In some embodiments, the L-carnitine content for canines can be minimally about 50 ppm, about 200 ppm, or about 300 ppm. For felines, slightly higher minimums of L-carnitine can be employed, for example about 100 ppm, about 200 ppm, or about 500 ppm. A non-toxic maximum quantity can be employed, for example, less than about 5,000 ppm. For canines lower quantities can be employed, for example, less than about 5,000 ppm. For canines a range can be from about 200 ppm to about 400 ppm. For felines a range can be from about 400 ppm to about 600 ppm.

In various embodiments, from about 1 ppm up to about 15 ppm beta carotene, from about 0.1 up to about 5 ppm selenium, at least about 5 ppm of lutein, at least about 25 ppm of tocotrienol(s), at least about 25 ppm of coenzyme Q10, at least about 50 ppm of S-adenosylmethionine, at least about 500 ppm of taurine, at least about 25 ppm of soy isoflavone(s), at least about 50 ppm of N-acetylcysteine, at least about 50 ppm of glutathione, at least 50 ppm of *Ginkgo biloba* extract can be used independently or in various combinations.

The total amount of the one or more antioxidants in the composition is sufficient to effect modulation of expression of one or more genes or gene products in the mammal. As used herein, "modulating" expression refers to altering the level of expression of one or more genes or gene products. Alteration in expression of a gene or gene product includes up-regulation (or induction) such that the gene or gene product is expressed at greater levels than normally found in the mammal, or found in the absence of antioxidant(s) added to the food of the mammal. Alternatively, alteration in expression can be down-regulation (or repression) of the gene or gene product such that the gene or gene product is expressed at lower levels than normally found in the mammal, or found in the absence of antioxidant(s) added to the food of the mammal.

In some embodiments, a gene that can be modulated can be a cytochrome P450 family gene, an apolipoprotein family gene, a gene encoding one or more products which regulate hemodynamic properties, a heat shock protein family gene, a gene encoding one or more products indicative of DNA damage, a gene encoding one or more products that regulate cell cycle, a pro-inflammatory gene, a gene encoding one or more proteins associated with a chromaffin secretory pathway, a gene encoding one or more products that regulate gene transcription, an NF-KB pathway gene, a gene encoding one or more products related to immune function, a gene encoding one or more glycolytic enzymes, a gene encoding one or more mitochondrial oxidative pathway proteins, or a gene encoding one or more ribosomal proteins.

In some embodiments, a combination of the above genes can be modulated.

In some embodiments, a cytochrome P450 family gene can be, for example, P450, family 2, subfamily b, polypeptide 10 (Cyp2b10), P450, family 2, subfamily c, polypeptide 70 (Cyp2c70), P450, family 2, subfamily c, polypeptide 37 (Cyp2c37), P450, family 2, subfamily a, polypeptide 12 (Cyp2a12), P450, family 2, subfamily c, polypeptide 40 (Cyp2c40), P450, family 3, subfamily a, polypeptide 11 (Cyp3a11), P450, family 3, subfamily a, polypeptide 13 (Cyp3a15), P450, family 3, subfamily a, polypeptide 16 (Cyp3a16), P450, family 3, subfamily a, polypeptide 25 (Cyp3a25), P450, family 2, subfamily a, polypeptide 4 (Cyp2a4), or P450, family 4, subfamily a, polypeptide 10 (Cyp4a10).

In some embodiments, an apolipoprotein family gene can be, for example, apolipoprotein C-II (Apoc2), apolipoprotein A-I (Apoa1), apolipoprotein A-II (Apoa2), apolipoprotein A-V (Apoa5), or apolipoprotein H (Apoh).

In some embodiments, a gene encoding one or more products which regulate hemodynamic properties can be, for example, a gene encoding fibrinogen, alpha polypeptide (Fga), coagulation factor X (F10), angiogenin (Ang), paraoxonase 1 (Pon1), Kininogen (Kng), coagulation factor XII, beta subunit (F13b), low density lipoprotein receptor-related protein 2 (Lrp2), coagulation factor V(F5), plasminogen (Plg), coagulation factor II (F2), angiotensinogen (Agt), or fibrinogen, B beta polypeptide (Fgb).

In some embodiments, a heat shock protein gene can be, for example, a gene encoding heat shock protein (Hsp105), chaperonin subunit 5 (epsilon) (Cct5), chaperonin subunit 8 (theta) (Cct8), DnaJ (Hsp40) homolog, subfamily A, member 1 (Dnaja1), DnaJ (Hsp40) homolog, subfamily C, member 2 (Dnajc2), DnaJ (Hsp40) homolog, subfamily C, member 7 (Dnajc7), heat shock 70 kD protein 5 (glucose-regulated protein) (Hspa5), heat shock protein (Hsp105), heat shock protein 1, alpha (Hspca), heat shock protein 1, beta (Hspcb), heat shock protein 1A (Hspa1a), heat shock protein 1B (Hspa1b), heat shock protein 4 (Hspa4), heat shock protein 4 (Hspa4), heat shock protein 8 (Hspa8), osmotic stress protein (Osp94), protein disulfide isomerase-related protein (P5-pending), or stress-induced phosphoprotein 1 (Stip1).

In some embodiments, a gene encoding one or more products indicative of DNA damage can be, for example, a gene encoding ataxia telangiectasia mutated homolog (human) (Atm), damage specific DNA binding protein 1 (Ddb1), excision repair cross-complementing rodent repair deficiency, complementation group 3 (Ercc3), huntingtin-associated protein 1 (Hap1), mutS homolog 2 (*E. coli*)

(Msh2), myeloid ecotropic viral integration site-related gene 1 (Mrg1), neuroblastoma ras oncogene (Nras), RAD21 homolog (*S. pombe*) (Rad21), retinoblastoma 1 (Rb1), retinoblastoma binding protein 4 (Rbbp4), retinoblastoma binding protein 7 (Rbbp7), retinoblastoma binding protein 9 (Rbbp9), spinocerebellar ataxia 2 homolog (human) (Sca2), X-linked myotubular myopathy gene 1 (Mtm1), or X-ray repair complementing defective repair in Chinese hamster cells 5 (Xrcc5).

In some embodiments, a gene encoding one or more products that regulate cell cycle can be, for example, cyclin G1 (Ccng1), cyclin D2 (Ccnd2), CDC23 (cell division cycle 23, yeast, homolog) (Cdc23), cyclin D3 (Ccnd3), cyclin-dependent kinase 5 (Cdk5), p21 (CDKN1A)-activated kinase 2 (Pak2), RAS p21 protein activator 1 (Rasa1), cyclin-dependent kinase 8 (Cdk8), CDC42 effector protein (Rho GTPase binding) 4 (Cdc42ep4), caspase 8 (Casp8), caspase 4, apoptosis-related cysteine protease (Casp4), caspase 12 (Casp12), Bcl-associated death promoter (Bad), Bcl2-like 2 (Bcl2l2), programmed cell death 6 interacting protein (Pdcd6lp), programmed cell death 8 (Pdcd8), programmed cell death 2 (Pdcd2), annexin A1 (Anxa1), annexin A2 (Anxa2), or signal-induced proliferation associated gene 1 (Sipa1).

In some embodiments, a pro-inflammatory gene can be, for example, a gene encoding histidine decarboxylase (Hdc), activated leukocyte cell adhesion molecule (Alcam), protocadherin alpha 4 (Pcdha4), neutrophil cytosolic factor 4 (Ncf4), mast cell protease 5 (Mcpt5), cathepsin S (Ctss), cadherin 2 (Cdh2), junction cell adhesion molecule 3 (Jcam3), macrophage expressed gene 1 (Mpeg1), cathepsin B (Ctsb), calcyclin binding protein (Cacybp), paraoxonase 2 (Pon2), P lysozyme structural (Lzp-s), Leukotriene B4 12-hydroxydehydrogenase (Ltbdh), lysosomal acid lipase 1 (Lip1), lysozyme (Lyzs), or histidine ammonia lyase (Hal).

In some embodiments, a gene encoding one or more proteins associated with a chromaffin secretory pathway can be, for example, vesicular membrane protein p24 (Vmp), $Ca^{2+}$-dependent activator protein for secretion (Cadps), secretogranin III (Scg3), synaptotagmin 4 (Syt4), exportin 1, CRM1 homolog (yeast) (Xpo1), synaptotagmin-like 4 (Syt14), glutamate receptor, ionotropic, AMPA2 (alpha 2) (Gria2), synaptosomal-associated protein 25 (Snap25), neuropilin (Nrp), synaptosomal-associated protein 25 binding protein (Snap25 bp), synaptosomal-associated protein 91 (Snap91), synaptotagmin 1 (Syt1), synaptophysin (Syp), dynamin 1-like (Dnm1l), cytotoxic granule-associated RNA binding protein 1 (Tia1), rabaptin 5 (RabSep-pending), dynamin (Dmn), microtubule-associated protein tau (Mapt), syntaxin 4A (placental) (Stx4a), secretory granule neuroendocrine protein 1, 7B2 protein (Sgne1), vesicular membrane protein p24 (Vmp), coronin, actin binding protein 1A (Coro1a), chromogranin A (Chga), synaptotagmin-like 4 (Sytl4), coatomer protein complex subunit alpha (Copa), dynein, cytoplasmic, light chain 2A (Dncl2a), coatomer protein complex, subunit gamma 1 (Copg1), vesicle-associated membrane protein 4 (Vamp4), sec 13-like protein (Sec 131-pending), calnexin (Canx), syntaxin binding protein 3 (Stxbp3), vacuolar protein sorting 16 (yeast) (Vps16), SEC22 vesicle trafficking protein-like 1 (*S. cerevisiae*) (Sec22l1), coatomer protein complex, subunit beta 2 (beta prime) (Copb2), proteoglycan, secretory granule (Prg), syntaxin 6 (Stx6), tubulin, alpha 3 (Tuba3), capping protein alpha 1 (Cappa1), or secretory carrier membrane protein 1 (Scamp 1).

In some embodiments, a gene encoding one or more products that regulate gene transcription can be, for example, a gene encoding splicing factor 3b, subunit 1 (Sf3b1), Trf (TATA binding protein-related factor)—proximal p (Trfp), RNA binding motif protein 10 (Rbm10), transcription factor 4 (Tcf4), transcription factor 12 (Tcf12), polymerase (DNA directed), beta (Polb), CCR4-NOT transcription complex, subunit 2 (Cnot2), cleavage stimulation factor, 3' pre-RNA, subunit 2, 64 kDa, tau variant (Cstf2tau variant), splicing factor, arginine/serine-rich 1 (ASF/SF2) (Sfrs1), general transcription factor II I (Gtf2i), YY1 transcription factor (Yy1), CCAAT/enhancer binding protein alpha (C/EBP), related sequence 1 (Cebpa-rs1), PRP4 pre-mRNA processing factor 4 homolog B (yeast) (Prpf4b), splicing factor 3a, subunit 3, 60 kDa (St3a3), or polymerase (RNA) II (DNA directed) polypeptide H (Polr2h).

In some embodiments, an NF-KB pathway gene can be serum amyloid A 3 (Saa3), lymphotoxin B (Ltb), nuclear factor of kappa light polypeptide gene enhancer in B-cells 2, p49/p100 (Nfkb2), nuclear factor of kappa light chain gene enhancer in B-cells inhibitor, alpha (Nfkbia), CCPAT/enhancer binding protein alpha (C/EBP), related sequence 1 (Cebpa-rs1), tumor necrosis factor receptor superfamily, member 1a (Tnfrsf1a), or nuclear factor of kappa light chain gene enhancer in B-cells 1, p105 (Nfkb1).

In some embodiments, a gene encoding one or more products related to immune function can be a gene encoding immunoglobulin lambda chain, variable 1 (Igl-V1), histocompatibility 2, class II, locus Mb1 (H2-DMb1), lymphotoxin B (Ltb), chemokine (C-C motitf ligand 5 (Ccl5), immunoglobulin heavy chain 4 (serum IgG1) (Igh-4), interferon-induced protein with tetratricopeptide (Ifit2), histocompatibility 2, class II, locus Mb2 (H2-Dib2), orosomucoid 2 (Orm2), immunoglobulin heavy chain 6 (heavy chain of Igl) (Igh-6), CD52 antigen (CdS2), immunoglobulin kappa chain variable 8 (V8) (Igk-V8), CD24a antigen (Cd24a), chemokline (C-X-C motif) receptor 4 (Cxcr4), interferon regulatory factor 4 Irf4), neutrophil cytosolic factor 1 (Ncf1), lymphoblastomic leukemia (Lyl1), lymphocyte specific 1 (Lsp1), chemokine (C-X-C motif) ligand 13 (Cxcl13), serum amyloid A 2 (Saa2), or CD79B antigen (Cd79b).

In some embodiments, a gene encoding one or more glycolytic or mitochondrial oxidative enzymes can be, for example, a gene encoding pyruvate dehydrogenase kinase, isoenzyme 3 (Pdk3), pyruvate kinase, muscle (Pkm2), phosphofructokinase platelet (Pfkp), adenylosuccinate lyase (Adsl), aldolase 1, A isoform (Aldo1), hexokinase 1 (Hk1), glyceraldehyde-3-phosphate dehydrogenase (Gapd), phosphofructokinase, liver, B-type (Pfd1), glucose phosphate isomerase 1 (Gpi1), 6-phosphogluconolactonase (Pgls), transaldolase 1 (Taldo1), Transketolase (Tkt), 2,3-bisphosphoglycerate mutase (Bpgm), ATP citrate lyase (Acly), ATPase, H+ transporting, V0 subunit B (Atp6v0b), ATPase, H+ transporting, V0 subunit D isoform 1 (Atp6v0d1), cytochrome c oxidase subunit VIIe polypeptide 2-like (Cox7a21), ATPase, H-transporting, V1 subunit A, isoform 1 (Atp6v1a1), NADH dehydrogenase (ubiquin-one) 1 alpha subcomplex, 3 (Ndufa3), or enolase 1, alpha non-neuron (Eno 1).

In some embodiments, a gene encoding one or more ribosomal proteins can be, for example, a gene encoding mitochondrial ribosomal protein L54 (Mrpl54), ribosomal protein S11 (Rps11), ribosomal protein S19 (Rps19), mitochondrial ribosomal protein L44 (Mrpl44), ribosomal protein L13a (Rpl13a), ribosomal protein S8 (Rps8), ribosomal protein S12 (Rps12), ribosomal protein S26 (Rps26), ribosomal protein L27a (Rpl27a), ribosomal protein L8 (Rpl8), ribosomal protein S23 (Rps23), ribosomal protein L37

(Rpl37), ribosomal protein L13 (Rpl13), ribosomal protein S3 (Rps3), ribosomal protein L3 (Rpl3), ribosomal protein L18 (Rpl18), mitochondrial ribosomal protein S15 (Mrpsl5), eukaryotic translation initiation factor 3, subunit 7 (zeta) (Eif3s7), ribosomal protein S5 (Rps5), ribosomal protein L36 (Rpl36), ribosomal protein S4, X-linked (Rps4x), or ribosomal protein L19 (Rpl19).

In various embodiments, this invention contemplates increasing expression of a cytochrome P450 family gene, increasing expression of an apolipoprotein family gene, increasing expression of a gene encoding product(s) which regulate hemodynamic properties, decreasing expression of a heat shock protein family gene, decreasing expression of a gene product that indicative of DNA damage, decreasing expression of a gene whose product(s) regulate cell cycle, decreasing expression of a pro-inflammatory gene, decreasing expression of a gene encoding protein associated with chromaffin secretory pathways, decreasing expression of a gene whose expression product(s) regulate gene transcription, decreasing expression of an NF-KB pathway gene, decreasing expression of a gene encoding product(s) related to immune function, decreasing expression of a gene encoding a glycolytic enzyme(s), decreasing expression of a gene encoding mitochondrial oxidative pathway protein(s), or decreasing expression of a gene encoding ribosomal protein(s).

In various embodiments, expression of a gene (or gene product) can be modulated in any number of different tissues and organs, for example, adrenal gland, liver, or cerebral cortex. In other embodiments, expression of a gene (or gene product) is modulated in adrenal gland, in the liver or in the cerebral cortex. In further embodiments, this invention provides methods for altering behavior in a senescent mammal comprising administering to the senescent mammal a composition comprising one or more antioxidants.

In some embodiments, this invention provides methods for treating, preventing, inhibiting, or reversing deterioration of cognitive and/or physical function of a mammal associated with aging comprising administering to the mammal one or more antioxidants whose total amount is effective to modulate expression of one or more genes. In some embodiments, those methods improve the oxidative status of the mammal.

Cognitive function associated with aging can refer to symptoms of mental deterioration, for example, memory loss or impairment, learning impairment, disorientation, and reduction in mental alertness.

Physical function associated with aging can include symptoms of, for example, deterioration or impairment of muscle function, deterioration or impairment of vascular function, deterioration or impairment of vision, deterioration or impairment of hearing, deterioration or impairment of olfaction, deterioration or impairment of skin or coat quality, deterioration of bone and joint health, deterioration of renal health, deterioration or impairment of gut function, deterioration or impairment of immune function, deterioration or impairment of insulin sensitivity, and/or deterioration or impairment of inflammatory responses.

In some embodiments, this invention provides methods for assessing oxidative status of a mammal. These methods can comprise determining the level of expression of one or more genes, for example a gene described herein. In various embodiments, those methods can further comprise determining the level of expression of at least one of those genes in one or more tissues, for example, adrenal gland, liver, or cerebral cortex.

In some embodiments, this invention provides methods for mimicking the effects of caloric restriction on gene expression in a mammal. In some aspects, caloric restriction reduces damage from chemical metabolic processes, particularly oxidative damage. In other aspects, caloric restriction is useful in weight control. These methods can comprise administering to the mammal one or more antioxidants in an amount effective to modulate one or more genes encoding glycolytic enzyme(s) or protein(s) associated with mitochondrial oxidative pathways. Therefore, the methods of this invention are also useful in controlling the body weight of mammals. As used herein, "control" of body weight may involve weight reduction, weight gain, or current weight maintenance.

In some embodiments, the present invention provides methods for repressing immune-function related genes and can be used for treating, preventing, or inhibiting inflammation and methods for decreasing DNA damage as evidenced by a decrease in DNA repair mechanisms induced.

In some embodiments, administration of the compositions of this invention can decrease cell death as evidenced by decreased expression levels of heat shock protein mRNAs and cell cycle turnover mRNAs.

In some embodiments, administration of the compositions of this invention led to upregulation of genes such as members of the cytochrome p450 family in adrenal gland, thus increasing cytochrome P450 metabolism in adrenal tissue. Increased cytochrome P450 metabolism in adrenal gland may modulate the steroidogenic activity of the neuroendocrine/adrenal system to alleviate stress and anxiety in mammals.

In some embodiments, the invention provides methods for decreasing inflammatory response by down-regulation of inflammatory/immune-related genes. Administration of one or more antioxidants of this invention can alter hemodynamic properties by induction (up-regulation) of specific mRNAs. In other embodiments, the invention provides methods for treating, preventing, or inhibiting atherogenesis.

In various embodiments, this invention provides methods for evaluating the efficacy of a regimen for a mammal. The mammal can be any mammal that is undergoing the regimen, has undergone the regimen, or is being considered for the regimen. The regimen can be, for example, for improving or preventing deterioration of oxidative status; mimicking effects of caloric restriction; controlling body weight; treating, preventing, or inhibiting atherogenesis; treating, preventing, or inhibiting stress or anxiety; treating, preventing, or inhibiting inflammation; or altering behavior, for example improving or preventing deterioration of cognitive and/or physical function.

In some embodiments, the method of evaluating the efficacy of a regimen comprises determining the level of expression of one or more genes independently selected from a cytochrome P450 family gene, an apolipoprotein family gene, a gene encoding product(s) which regulate hemodynamic properties, a heat shock protein family gene, a gene encoding product(s) indicative of DNA damage, a gene encoding product(s) that regulate cell cycle, a pro-inflammatory gene, a gene encoding protein(s) associated with a chromaffin secretory pathway, a gene encoding product(s) that regulate gene transcription, an NF-KB pathway gene, a gene encoding product(s) related to immune function, a gene encoding glycolytic enzyme(s), a gene encoding mitochondrial oxidative pathway protein(s), and a gene encoding ribosomal protein(s); and comparing the expression level against a reference expression level, such that the expression level relative to the reference expression level is indicative of the efficacy of the regimen.

In various embodiments, the present teachings disclose a gene micro-array or proteomic screen. As used herein, the term "microarray" includes all the devices so called in Schena (ed.), DNA Microarrays: A Practical Approach (Practical Approach Series), Oxford University Press (1999) (ISBN: 0199637768); Nature Genet. 21(1)(suppl): 1-60 (1999); and Schena (ed.), Microarray Biochip: Tools and Technology, Eaton Publishing Company/BioTechniques Books Division (2000) (ISBN: 1881299376), which are incorporated herein by reference in their entireties. A micro-array of the present embodiments can be a micro-array configured for measuring expression of at least one gene indicative of the oxidative status of a mammal. In some embodiments, a micro-array can be configured to measure expression of a combination of genes indicative of oxidation status. A gene of these embodiments can be, for example, a gene described above. In some embodiments, a micro-array can be utilized to measure the expression of any of these genes or combinations of these genes.

As used herein, the term "proteomic" screen refers to protein analysis assays or protein binding screens, including assays or screens that involve many proteins in parallel. Proteomic approaches to protein analysis are described, for example, in BioTechniques 33: 1308-1316 (2002), the disclosure of which is incorporated herein by reference in its entirety.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "mammal" includes a plurality of such mammal. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compositions, compounds, methods, and other information reported therein that might be used with the present invention. However, nothing herein is to be construed as an admission that the invention is not entitled to antedate such disclosure by virtue of prior invention.

EXAMPLES

The invention can be further illustrated by the following examples of preferred embodiments thereof, although it will be understood that these examples are included merely for purposes of illustration and are not intended to limit the scope of the invention unless otherwise specifically indicated.

Example 1

This example illustrates mitigation of oxidative stress experienced by senescent mice fed various antioxidants as determined using biochemical measures of the ratio of reduced to oxidized glutathione (GSH:GSSG) as an indicator of oxidative stress.

GSH:GSSG ratios were measured by the method described in Jones, D. P., Redox Potential of GSH/GSSG Couple: Assay and Biological Significance, METHODS ENZYMOL., 348:93-112 (2002).

Senescence-Accelerated Mouse (SAM) strain, which provides a model system for aging, was obtained from Dr. T. Takeda and the council on SAM research, University of Tokyo, Tokyo, Japan (Takeda T. et al., Senescence-accelerated mouse (SAM): A novel murine model of senescence, Exp Gerontol, 32:105-109 (1997); Takeda T. et al., Pathobiology of the senescence-accelerated mouse (SAM), Exp Gerontol, 32:117-127 (1997); Takeda T., Senescence-accelerated mouse (SAM): A biogerontological resource in aging research, Neurobiol Aging, 20:105-110 (1999)).

C57BL6 mice are a long-lived lab mouse strain.

Unless indicated otherwise, all senescence-accelerated mice and C57BL6 mice were fed control food until they were switched to food A or food B. Those mice that were switched to food A or food B, were fed the corresponding food for at least 6 months (control mice were fed only control food). Unless indicated otherwise, food A was fed from 5 to 13 months of age, and food B was fed from 7 to 17 months of age. Unless indicated otherwise, the food compositions used were as listed in Table 2. The amounts in Table 2 are the amounts of the starting materials added to the composition expressed in percentage of the total weight.

TABLE 2

Food Compositions

| Ingredients | Control Food | Food A | Food B |
|---|---|---|---|
| Food Base A | 100 | ~100 | None added |
| Food Base B | None added | None added | ~95.7 |
| L-Carnitine | None added | 0.026 | None added |
| Lipoic Acid | None added | 0.014 | None added |
| Vitamin C | None added | 0.025 | 0.025 |
| 50% Vitamin E | None added | 0.110 | 0.110 |
| Broccoli | None added | None added | 1.5 |
| Rice Bran | None added | None added | 1 |
| Marine Oil | None added | None added | 0.88 |
| Glutamine Dipeptide | None added | None added | 0.5 |
| Methionine | None added | None added | 0.17 |
| Selenium - yeast | None added | None added | 0.03 |
| Algae | None added | None added | 0.025 |
| L-Threonine | None added | None added | 0.025 |
| 5% Lutein | None added | None added | 0.015 |
| 5% Lycopene | None added | None added | 0.015 |
| 8% Astaxanthin | None added | None added | 0.0094 |
| 10% Beta-Carotene | None added | None added | 0.0075 |
| Curcumin | None added | None added | 0.005 |

Food Base A content: corn, poultry meal, rice, soybean mill run, corn gluten meal, soybean oil, fat, miscellaneous ingredients (i.e., vitamins, minerals, etc.).
Food Base B content: corn, soybean mill run, soybean meal, corn gluten meal, fat, miscellaneous ingredients (i.e., vitamins, minerals, etc.).

The major component differences between the control food, food A, and food B are presented in Table 3. The amounts in Table 3 are amounts added to the composition expressed in percentage of the total weight.

TABLE 3

Major Component Differences

| Ingredients | Control Food | Food A | Food B |
|---|---|---|---|
| Corn | 69.9 | 69.7 | 65.2 |
| Poultry Meal | 10.4 | 10.4 | None added |

TABLE 3-continued

Major Component Differences

| Ingredients | Control Food | Food A | Food B |
|---|---|---|---|
| Rice | 4 | 4 | None added |
| Soybean Mill Run | 4 | 4 | 3.9 |
| Soybean Meal | None added | None added | 8.75 |
| Corn Gluten Meal | 3.2 | 3.2 | 8.2 |
| Soybean Oil | 2.1 | 2.1 | None added |
| Fat | 2.1 | 2.1 | 4.1 |
| Broccoli | None added | None added | 1.5 |
| Rice Bran | None added | None added | 1 |
| Marine Oil | None added | None added | 0.88 |
| Glutamine Dipeptide | None added | None added | 0.5 |
| Methionine | None added | None added | 0.17 |
| Selenium - yeast | None added | None added | 0.03 |
| Algae | None added | None added | 0.025 |
| L-Threonine | None added | None added | 0.025 |
| 5% Lutein | None added | None added | 0.015 |
| 5% Lycopene | None added | None added | 0.015 |
| 8% Astaxanthin | None added | None added | 0.0094 |
| 10% Beta-Carotene | None added | None added | 0.0075 |
| Curcumin | None added | None added | 0.005 |
| Choline Chloride | 0.26 | 0.26 | 0.5 |

Analytical analysis show that the control food contained 17% protein, 10% fat, approximately 200 ppm vitamin E, and <32 ppm vitamin C. Analytical analysis showed that food A contained 17% protein, 10% fat, approximately 500 ppm vitamin E, approximately 80 ppm vitamin C, approximately 300 ppm L-carnitine, and approximately 125 ppm lipoic acid. Analytical analysis showed that food B contained 19% protein, 10% fat, approximately 500 ppm vitamin E, and approximately 80 ppm vitamin C.

The effects of antioxidant-enriched foods A and B on oxidative stress were determined. In one experiment, the concentration of reduced glutathione (GSH) and oxidized glutathione (GSSG), a measure of oxidative balance, was measured in the plasma of senescence accelerated mice on the control food or food A, and a group of normal mice (C57BL/6) on control food. The GSH:GSSG ratio for the senescence accelerated mice fed control food was lower than the GSH:GSSG ratio for the C57BL/6 mice fed control food or the senescence accelerated mice fed food A. These results show that the senescence accelerated mice fed control food were under more oxidative stress than normal mice. The results also show that food A (i.e., a food supplemented with vitamin E, vitamin C, lipoic acid, and L-carnitine) mitigated this oxidative stress as shown by the improved GSH:GSSG ratios.

In another experiment, the effects of food B (i.e., a complex antioxidant-fortified food) on the GSH:GSSG ratios in plasma of senescence accelerated mice at 17 months of age was determined. Senescence accelerated mice fed food B had higher GSH:GSSG ratios than senescence accelerated mice fed control food. These results show that food B mitigates the oxidative stress experienced by senescence accelerated mice.

In another experiment, reduced to oxidized glutathione ratios were determined in tissues of senescence accelerated mice fed control food or food A. Compared to senescence accelerated mice fed control food, senescence accelerated mice fed food A had improved GSH:GSSG ratio in skeletal muscle. See Table 4. These results show that in addition to improving oxidative stress markers in plasma, supplemented food A also improves the same markers in at least one tissue, skeletal muscle, and is effective at intracellular buffering of oxidative stress.

TABLE 4

Concentrations of GSH and GSSG in Mitochondria of Senescence Accelerated Mice Fed Control Food and Food A

| Tissue | GSH (nmol/mg protein) | GSSG (nmol/mg protein) |
|---|---|---|
| Liver | | |
| Control Food | 7.172 ± 0.479 | 0.176 ± 0.025 |
| Food A | 7.213 ± 0.236 | 0.182 ± 0.027 |
| Kidney | | |
| Control Food | 1.787 ± 0.153 | 0.0083 ± 0.0002 |
| Food A | 1.883 ± 0.272 | 0.0102 ± 0.0019 |
| Heart | | |
| Control Food | 4.545 ± 0.327 | 0.298 ± 0.039 |
| Food A | 4.035 ± 0.446 | 0.281 ± 0.052 |
| Brain | | |
| Control Food | 4.216 ± 0.247 | 0.031 ± 0.005 |
| Food A | 4.286 ± 0.231 | 0.031 ± 0.004 |
| Skeletal Muscle | | |
| Control Food | 1.122 ± 0.092 | 0.102 ± 0.012 |
| Food A | 1.122 ± 0.101 | 0.040 ± 0.007[#] |

[#]Significant difference (P < 0.05) between control (n = 5) and experimental (n = 4) mice In another experiment, reduced to oxidized glutathione ratios were determined in tissues of senescence accelerated mice fed either control food or food B. Food B improved the GSH:GSSG ratio in all tissues (liver, kidney, heart, cerebral cortex, and skeletal muscle) compared to age- and sex-matched controls. See Table 5. These results show that in addition to improving GSH:GSSG ratios in plasma, food B also improves intracellular GSH:GSSG ratios. These results also show that food B is effective in mitigating the excessive production of free radicals in senescence accelerated mice, possibly resulting in improved health status with age.

TABLE 5

Concentrations of GSH and GSSG in Mitochondria of Senescence Accelerated Mice Fed Control Food and Food B

| Tissue | GSH (nmol/mg protein) | GSSG (nmol/mg protein) |
|---|---|---|
| Liver | | |
| Control Food (male) | 6.10 ± 0.07 | 0.175 ± 0.019 |
| Food B (male) | 5.65 ± 0.36 | 0.162 ± 0.019 |
| Control Food (female) | 6.20 ± 0.53 | 0.428 ± 0.063 |
| Food B (female) | 6.74 ± 0.35 | 0.175 ± 0.024[#] |
| Kidney | | |
| Control Food (male) | 2.23 ± 0.27 | 0.021 ± 0.004 |
| Food B (male) | 2.86 ± 0.27[#] | 0.018 ± 0.002 |
| Control Food (female) | 2.42 ± 0.48 | 0.021 ± 0.001 |
| Food B (female) | 3.72 ± 0.20[#] | 0.012 ± 0.001[#] |
| Heart | | |
| Control Food (male) | 4.25 ± 0.45 | 0.322 ± 0.009 |
| Food B (male) | 7.09 ± 0.44[#] | 0.290 ± 0.022[#] |
| Control Food (female) | 4.08 ± 0.28 | 0.349 ± 0.011 |
| Food B (female) | 4.55 ± 0.44 | 0.319 ± 0.002[#] |
| Brain | | |
| Control Food (male) | 4.86 ± 0.15 | 0.059 ± 0.001 |
| Food B (male) | 6.02 ± 0.32[#] | 0.030 ± 0.001[#] |

TABLE 5-continued

Concentrations of GSH and GSSG in Mitochondria of Senescence Accelerated Mice Fed Control Food and Food B

| Tissue | GSH (nmol/mg protein) | GSSG (nmol/mg protein) |
|---|---|---|
| Control Food (female) | 5.29 ± 0.26 | 0.034 ± 0.002 |
| Food B (female) | 6.23 ± 0.20# | 0.027 ± 0.001# |
| Skeletal Muscle | | |
| Control Food (male) | 1.76 ± 0.10 | 0.113 ± 0.021 |
| Food B (male) | 2.49 ± 0.40# | 0.125 ± 0.027 |
| Control Food (female) | 1.80 ± 0.06 | 0.147 ± 0.016 |
| Food B (female) | 2.43 ± 0.39# | 0.098 ± 0.010# |

Significant difference (P < 0.05, n = 4) between control and experimental groups of senescence accelerated mice Example 2

The genomic response to antioxidant(s) in senescence accelerated mice fed various antioxidant-comprising foods were determined by mRNA expression analysis.

Three groups of 5-6 senescence-accelerated mice were fed control food, food A, or food B as explained in Example 1 above. The compositions of the foods were as in Example 1 above as well.

Molecular biology techniques follow standard protocols well known to skilled artisans, such as those set forth in Sambrook et al., Molecular Cloning: A Laboratory Manual, 2nd ed. Cold Spring Harbor Laboratory Press, Cold Spring Harbor, N.Y. (1989). Tissue was obtained from mice, and RNA was extracted from that tissue. The extracted RNA was pooled by tissue (liver, adrenal gland, and cerebral cortex) and food (control, A, or B), resulting in a total of nine pooled RNA samples. The pooled total RNA samples were further processed to obtain gene (mRNA) expressions using Mu74Av2 high density oligonucleotide arrays (Mu74Av2 GeneChip, Affymetrix, Santa Clara, Calif.) according to the manufacturer's instructions. Microarray Analysis Suite (MAS) 5.0 (Affymetrix) was used to calculate fluorescence intensities of hybridized, biotinylated RNA fragments. All statistical analyses were performed with the MAS 5.0. Each mRNA was analyzed with 32 different probes—16 probes for specific binding, and 16 for non-specific binding. All signals with a p<0.05 were considered significant and were used for the analysis of biological effects. Approximately 4,000-8,000 genes were detected. The detection value ranged from 10-6,000. The range of p values was 0.0001-0.05. Significant differences were determined by comparing the intensities of all 32 probes for the gene in one group with those in the other group. p values <0.05 were considered significantly different.

The effect of foods A and B on overall gene expression in various tissues was determined. Table 6 shows the total numbers of gene detected by the GeneChip assay.

TABLE 6

Total Numbers of Genes Detected by the GeneChip Assay

| Food | Adrenal gland | Cortex | Liver |
|---|---|---|---|
| Control | 7218 | 6062 | 6094 |
| Food A | 6809 | 6175 | 4389 |
| Food B | 7288 | 6206 | 4402 |

The effects of foods A and B were compared with the gene expression profile of the three tissues obtained from mice fed control food. The differences in the detection of the total numbers of genes in the tissues from the three food groups can be partially explained by net repression of genes in the affected tissue.

Similar numbers of genes were detected in the three tissues from mice fed control food. In liver and adrenal gland, fewer genes (28% and 6%, respectively) were detected in mice fed food A, suggesting a net repression of gene expression. Food B had a similar effect on the activity of the liver genome. With respect to the adrenal gland genome, food B showed a net induction in the activity of the genome. The activities of the liver genome were similarly affected by foods A and B. Cerebral cortex from the three food groups of mice was least responsive to foods A and B, suggesting a greater stability of the cerebral genome to the dietary constituents of the two foods. This may be attributed to the permeability barrier imposed by the "blood brain barrier" to the dietary antioxidants and their putative metabolic products.

To conclude, the above studies showed different effects of foods A and B on the activity of the adrenal genome and similar effects of foods A and B on the activity of the liver and cerebral cortex genomes. See generally FIG. 1.

Example 3

The effects of foods A and B on expression of various classes of genes in various tissues of senescence accelerated mice were determined using the GeneChip assay described above.

Figure 2:
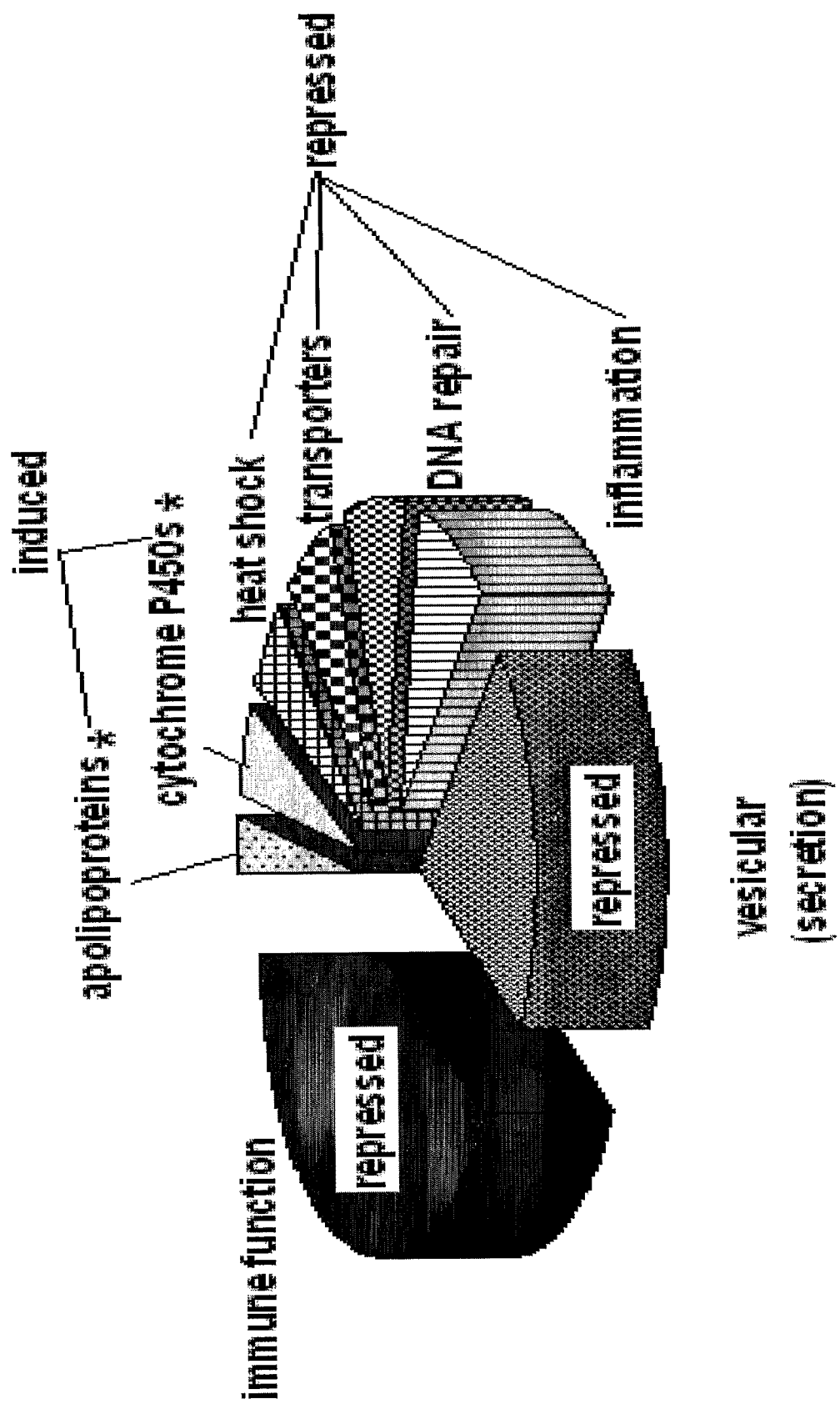
FIG. 2 shows the functional classes of adrenal gland genes whose expression is modulated in mice fed foods A and B and the relative distribution of those genes.
Figure 3:
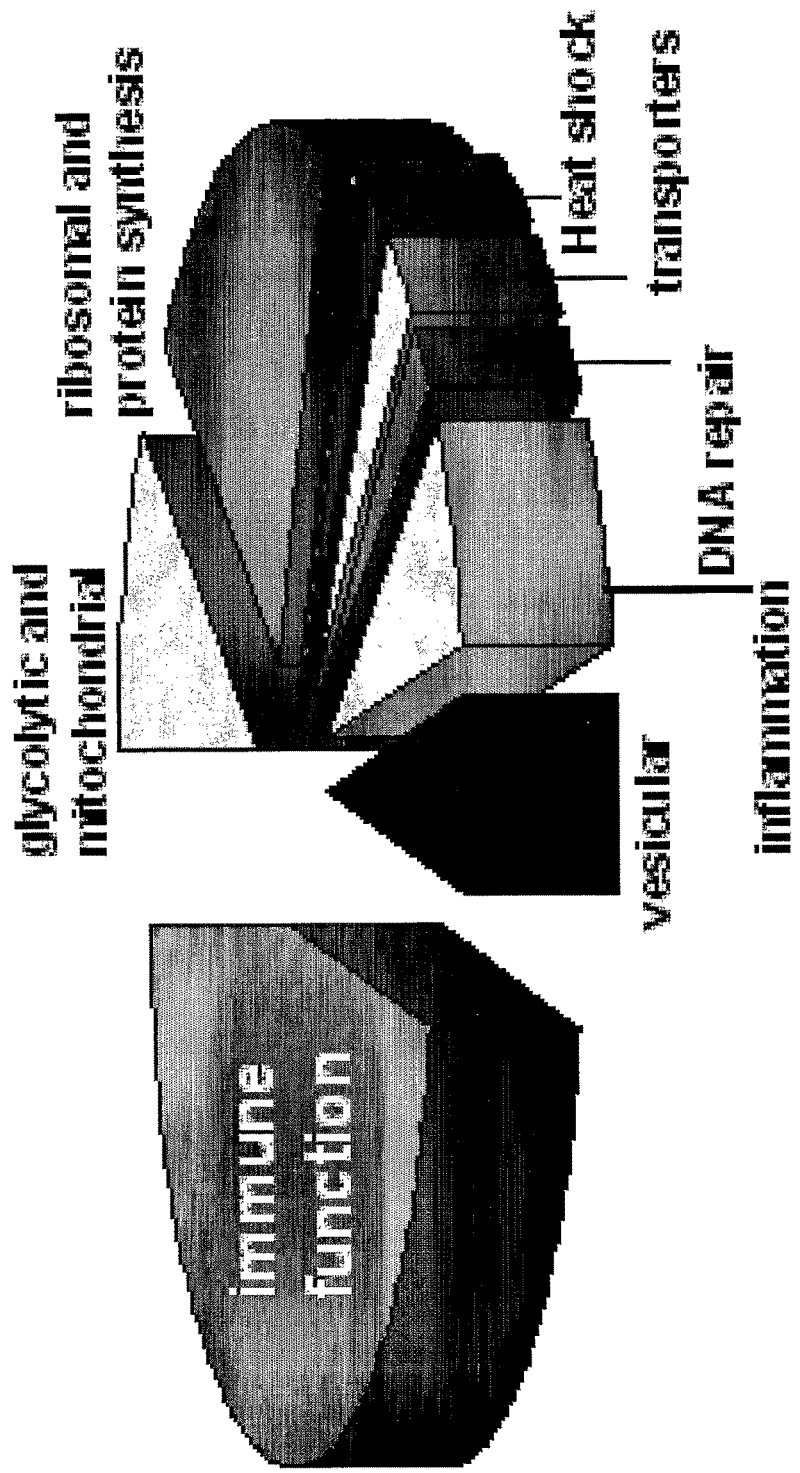
FIG. 3 shows the functional classes of hepatic genes whose expression is modulated in mice fed foods A and B and the relative distribution of those genes.
Figure 4:
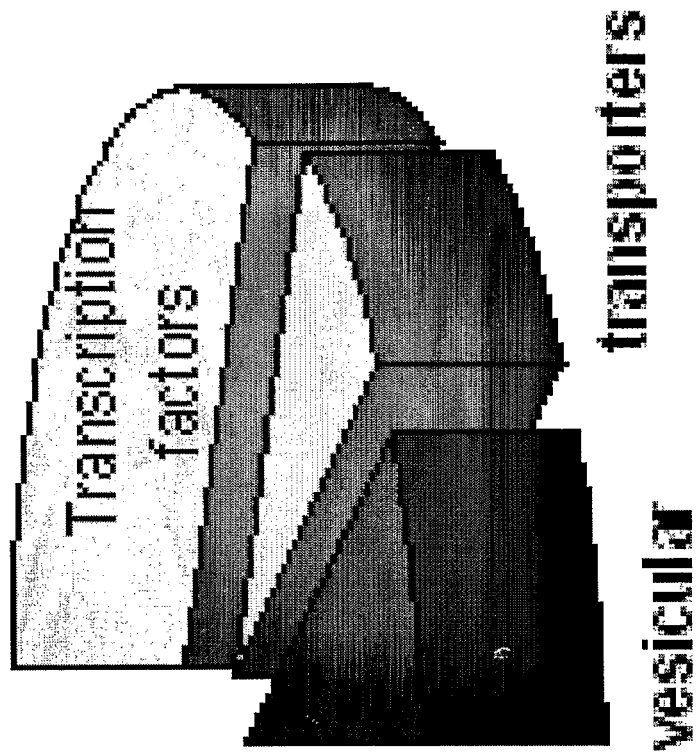
FIG. 4 shows the functional classification of cerebral cortex genes whose expression is modulated in mice fed food A and the relative distribution of those genes.
Figure 4:
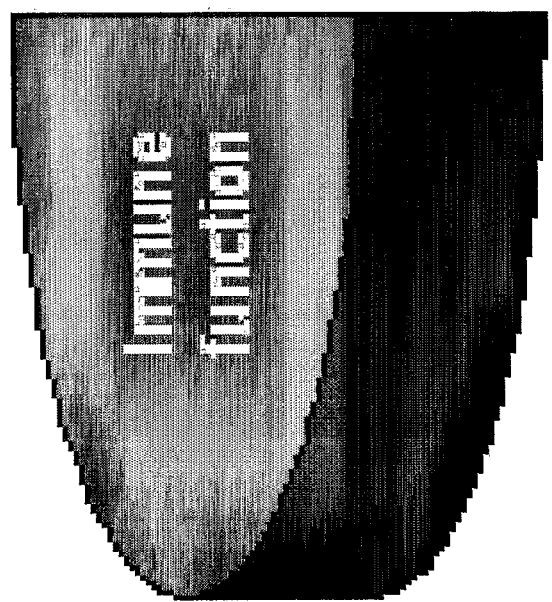

FIGS. 2, 3, and 4 summarize the functional classes of genes whose expression is modulated in mice fed foods A and B and the relative contribution of those genes to the changes in gene profiles.

FIGS. 2 and 3 show an overview of the functional classes of adrenal gland and liver genes, respectively, that are affected by foods A and B and their relative distributions. Foods A and B had repressive effects on the functional groups of genes illustrated in FIGS. 2 and 3. Largest numbers of the affected genes regulate immune functions. Similarly, genes that regulate inflammation, secretion, response to DNA damage, and heat shock were also down regulated by foods A and B in liver and the adrenal gland. Genes that encode enzymes of glycolysis, mitochondrial oxidations, and protein synthesis were downregulated in the liver by foods A and B.

Foods A and B affected secretory pathways. Since liver and adrenal glands are secretory organs, the results suggest that those foods may regulate the composition of blood and lymph and the functions of other organs.

FIG. 4 shows the functional classification and relative distribution of differentially expressed genes in the cerebral cortex of mice fed food A. A similar distribution of differentially expressed genes was detected in the cerebral cortex of mice fed food B. DNA repair and heat shock protein families of genes were not repressed in the cerebral cortex of mice fed foods A and B (although those genes were repressed in liver and adrenal gland of mice fed foods A and B).

Example 4

The effects of foods A and B on expression of various classes of genes in adrenal gland of senescence accelerated mice were determined by the GeneChip assay described above.

Comparative analysis of gene expression profiles suggest that the adrenal gland is an important "sensor" of micronutrient status. Since the gland is an integral component of the hypothalamic-pituitary-adrenal axis, it may also be an important effector of antioxidant micronutrients.

Cytochrome P450 Family: Functional gene analysis showed that members of the cytochrome P450 family were induced by foods A and B. The list of affected members of this family is shown in Table 7.

TABLE 7

Induction of Cytochrome P450 Family Member in Adrenal Gland

| Name of Cytochrome P450 | Food A FOLD Change | Food B FOLD Change | Gene SYMBOL |
| --- | --- | --- | --- |
| P450, family 2, subfamily b, polypeptide 10 | 3.0 | 2.6 | Cyp2b10 |
| P450, family 2, subfamily c, polypeptide 70 | 3.5 | 6.5 | Cyp2c70 |
| P450, family 2, subfamily c, polypeptide 37 | 3.7 | 8.0 | Cyp2c37 |
| P450, family 2, subfamily a, polypeptide 12 | 4.3 | 8.0 | Cyp2a12 |
| P450, family 2, subfamily c, polypeptide 40 | 4.9 | 7.5 | Cyp2c40 |
| P450, family 3, subfamily a, polypeptide 11 | 5.3 | 9.8 | Cyp3a11 |
| P450, family 3, subfamily a, polypeptide 13 | 7.5 | 5.3 | Cyp3a15 |
| P450, family 3, subfamily a, polypeptide 16 | 7.5 | 13.0 | Cyp3a16 |
| P450, family 3, subfamily a, polypeptide 25 | 9.2 | 13.0 | Cyp3a25 |
| P450, family 2, subfamily a, polypeptide 4 | 13.9 | 21.1 | Cyp2a4 |
| P450, family 4, subfamily a, polypeptide 10 | 24.3 | 29.9 | Cyp4a10 |

These results show that foods A and B induced cytochrome P450 family of genes. Products of cytochrome P450 family of genes play an important role in the metabolism of xenobiotics, arachidonic acid, and steroids. This suggests that foods A and B can modulate steroidogenic activity of this vital neuro-endocrine organ.

Apolipoprotein Family: Functional gene analysis showed that members of the apolipoprotein family were induced by foods A and B. The list of affected members of this family is shown in Table 8.

TABLE 8

Induction of Apolipoprotein Family Member in Adrenal Gland

| Gene Name | Food A FOLD Change | Food B FOLD Change | Gene SYMBOL |
| --- | --- | --- | --- |
| apolipoprotein C-II | 2.8 | 3.5 | Apoc2 |
| apolipoprotein A-V | 4.6 | 6.5 | Apoa5 |
| unnamed apolipoprotein similar to apolipoprotein B-100 | 6.1 | 4.3 | — |
| apolipoprotein A-I | 6.1 | 5.7 | Apoa1 |
| apolipoprotein A-II | 6.5 | 9.8 | Apoa2 |
| apolipoprotein H | 13.0 | 13.9 | Apoh |

These results show that foods A and B induce apolipoprotein family of genes. The apolipoproteins play a coordinately important role in the metabolism of steroids. This suggests that foods A and B can modulate steroidogenic properties.

Genes Encoding Products that Regulate Hemodynamic Properties: Functional gene analysis showed that genes that regulate hemodynamic properties of blood were induced by foods A and B. The list of affected members of this family is shown in Table 9.

TABLE 9

Induction of Genes That Regulate Hemodynamic Properties in Adrenal Gland

| Gene Name | Food A FOLD change | Food B FOLD change | Gene Symbol |
| --- | --- | --- | --- |
| fibrinogen, alpha polypeptide | 2.0 | 3.0 | Fga |
| coagulation factor X | 2.6 | 4.0 | F10 |
| angiogenin | 3.2 | 3.2 | Ang |
| paraoxonase 1 | 4.0 | 7.5 | Pon1 |
| Kininogen | 4.3 | 4.0 | Kng |
| coagulation factor XII, beta subunit | 4.6 | 6.5 | F13b |
| low density lipoprotein receptor-related protein 2 | 5.3 | 4.3 | Lrp2 |
| coagulation factor V | 6.5 | 9.2 | F5 |
| Plasminogen | 9.2 | 10.6 | Plg |
| coagulation factor II | 9.2 | 13.9 | F2 |
| Angiotensinogen | 9.8 | 9.2 | Agt |
| fibrinogen, B beta polypeptide | 9.8 | 12.1 | Fgb |

These results show that foods A and B induce genes that encode products that regulate hemodynamic properties. Moreover, anti-atherogenic effects of foods A and B are suggested by induction of mRNA for Paraoxanase 1. High plasma level of paraoxonase 1 are associated with low incidence of atherogenesis.

Genes Encoding Heat Shock Proteins: Functional gene analysis showed that expression levels of a family of genes encoding heat shock proteins were repressed. The list of affected members of this family is shown in Table 10.

TABLE 10

Repression of Genes for Heat Shock Proteins in Adrenal Gland

| Gene Name | Food A FOLD change* | Food B FOLD change | Gene Symbol |
| --- | --- | --- | --- |
| heat shock protein | −5.7 | NC[#] | Hsp105 |
| heat shock protein 1A | −4.0 | NC | Hspa1a |
| heat shock protein 1B | −3.0 | NC | Hspa1b |
| heat shock protein 4 | −3.0 | NC | Hspa4 |
| osmotic stress protein | −2.8 | NC | Osp94 |
| stress-induced phosphoprotein 1 | −2.6 | NC | Stip1 |
| heat shock protein 1, alpha | −2.5 | NC | Hspca |
| DnaJ (Hsp40) homolog, subfamily A, member 1 | −2.3 | NC | Dnaja1 |
| DnaJ (Hsp40) homolog, subfamily C, member 7 | −2.1 | NC | Dnajc7 |
| chaperonin subunit 8 (theta) | −2.1 | NC | Cct8 |
| chaperonin subunit 5 (epsilon) | −2.0 | NC | Cct5 |
| protein disulfide isomerase-related protein | −2.0 | NC | P5-pending |

*A hyphen before a number indicates a decrease. For example, a fold change of −5.7 indicates a 5.7-fold reduction in gene expression level.
[#]NC means that the change in gene expression level was less than twofold.

These results show that food A repressed heat shock protein genes. Induction of heat shock proteins is associated with increased physiological stress. The antioxidant effects of food A are suggested by decrease in the activities of the genes encoding heat shock proteins, chaperoning, and protein disulfide isomerases in adrenal gland and liver (see also Table 19). The results are notable in lacking effects on the expression of classical antioxidant genes such as those for SODs and catalases. The results also suggest that food A provided a protective effect against physiological stress.

Genes Encoding Products Indicative Of DNA Damage: Functional gene analysis showed that expression levels of a family of genes encoding products indicative of DNA damage were repressed. The list of affected members of this family is shown in Table 11.

TABLE 11

Repression of Genes Encoding Products That Indicate DNA Damage in Adrenal Gland

| Gene Name | Food A FOLD change* | Food B FOLD change | Gene Symbol |
|---|---|---|---|
| ataxia telangiectasia mutated homolog (human) | −3.0 | NC# | Atm |
| myeloid ecotropic viral integration site-related gene 1 | −2.5 | NC | Mrg1 |
| damage specific DNA binding protein 1 | −2.1 | 2.0 | Ddb1 |
| mutS homolog 2 (E. coli) | −2.1 | NC | Msh2 |
| X-ray repair complementing defective repair in Chinese hamster cells 5 | −2.1 | NC | Xrcc5 |
| retinoblastoma binding protein 9 | −2.1 | NC | Rbbp9 |
| X-linked myotubular myopathy gene 1 | −2.1 | NC | Mtm1 |
| excision repair cross-complementing rodent repair deficiency, complementation group 3 | −2.1 | NC | Ercc3 |
| retinoblastoma binding protein 7 | −2.0 | NC | Rbbp7 |
| spinocerebellar ataxia 2 homolog (human) | −2.0 | NC | Sca2 |
| huntingtin-associated protein 1 | −2.0 | NC | Hap1 |

*A hyphen before a number indicates a decrease. For example, a fold change of −3.0 indicates a 3.0-fold reduction in gene expression level.
NC means that the change in gene expression level was less than twofold.

These results show that food A repressed genes encoding products indicative of DNA damage. These results also suggest that food A decreases DNA damage in adrenal gland tissue.

Cell Cycle Genes: Functional gene analysis showed that expression levels of genes encoding products that regulate cell cycle were repressed. The list of affected members of this family is shown in Table 12.

TABLE 12

Repression of Genes Encoding Cell Cycle Proteins in Adrenal Gland

| Gene Name | Food A FOLD change* | Food B FOLD change | Gene Symbol |
|---|---|---|---|
| cyclin G1 | −2.6 | NC# | Ccng1 |
| cyclin D2 | −2.6 | NC | Ccnd2 |
| CDC23 (cell division cycle 23, yeast, homolog) | −2.3 | NC | Cdc23 |
| cyclin D3 | −2.1 | NC | Ccnd3 |
| cyclin-dependent kinase 5 | −2.1 | NC | Cdk5 |
| p21 (CDKN1A)-activated kinase 2 | −2.1 | NC | Pak2 |
| RAS p21 protein activator 1 | −2.1 | NC | Rasa1 |
| cyclin-dependent kinase 8 | −2.0 | 2.0 | Cdk8 |
| CDC42 effector protein (Rho GTPase binding) 4 | −2.0 | NC | Cdc42ep4 |
| caspase 8 | −3.2 | NC | Casp8 |
| caspase 4, apoptosis-related cysteine protease | −3.0 | NC | Casp4 |
| caspase 12 | −2.3 | NC | Casp12 |
| Bcl-associated death promoter | −2.3 | NC | Bad |
| Bcl2-like 2 | −2.1 | NC | Bcl2l2 |
| programmed cell death 6 interacting protein | −2.1 | NC | Pdcd6ip |
| programmed cell death 8 | −2.0 | NC | Pdcd8 |
| programmed cell death 2 | −2.0 | NC | Pdcd2 |
| annexin A1 | −2.0 | NC | Anxa1 |
| annexin A2 | −2.0 | NC | Anxa2 |
| signal-induced proliferation associated gene 1 | −2.6 | NC | Sipa1 |

*A hyphen before a number indicates a decrease. For example, a fold change of −2.6 indicates a 2.6-fold reduction in gene expression level.
NC means that the change in gene expression level was less than twofold.

These results show that food A repressed genes encoding products that regulate cell cycle.

Pro-inflamatory Genes: Functional gene analysis showed that expression levels of pro-inflammatory genes were repressed. The list of affected members of this family is shown in Table 13.

TABLE 13

Repression of Pro-Inflammatory Genes in Adrenal Gland

| Gene Name | Food A FOLD change* | Food B FOLD change* | Gene Symbol |
|---|---|---|---|
| histidine decarboxylase | −3.7 | NC# | Hdc |
| activated leukocyte cell adhesion molecule | −3.5 | NC | Alcam |
| protocadherin alpha 4 | −3.5 | NC | Pcdha4 |
| neutrophil cytosolic factor 4 | −3.5 | −2.0 | Ncf4 |
| mast cell protease 5 | −2.8 | NC | Mcpt5 |
| cathepsin S | −2.6 | NC | Ctss |
| cadherin 2 | −2.6 | NC | Cdh2 |
| junction cell adhesion molecule 3 | −2.6 | NC | Jcam3 |
| macrophage expressed gene 1 | −2.5 | NC | Mpeg1 |
| cathepsin B | −2.3 | NC | Ctsb |
| calcyclin binding protein | −2.3 | NC | Cacybp |
| paraoxonase 2 | −2.3 | NC | Pon2 |
| P lysozyme structural | −2.1 | NC | Lzp-s |
| Leukotriene B4 12-hydroxydehydrogenase | −2.1 | NC | Ltb4dh |
| lysosomal acid lipase 1 | −2.0 | NC | Lip1 |
| lysozyme | −2.0 | NC | Lyzs |
| histidine ammonia lyase | 2.3 | 3.2 | Hal |

*A hyphen before a number indicates a decrease. For example, a fold change of −3.7 indicates a 3.7-fold reduction in gene expression level.
NC means that the change in gene expression level was less than twofold.

These results show that genes related to inflammation were repressed by food A. Some of these effects may be attributed to a decrease in specific cell populations such as mast cells and invading macrophages. The repression of these genes may be partially accounted for by the repression of the genes that encode subunits of the pro-inflammatory transcription factors, nuclear factor kappa B (NF-kB), mitogen activated protein (MAP) kinases, and stimulator and activator of transcription (STAT).

Genes Encoding Proteins Associated With Chromaffin Secretory Pathways: Functional gene analysis showed that expression levels of genes that modulate the secretory pathways were repressed. The list of affected members of this family is shown in Table 14.

TABLE 14

Repression of Genes That Modulate Chromaffin Secretory Pathways in Adrenal Gland

| Gene Name | Food A FOLD change* | Food B FOLD change | Gene Symbol |
|---|---|---|---|
| vesicular membrane protein p24 | −4.3 | NC# | Vmp |
| Ca$^{2+}$-dependent activator protein for secretion | −3.7 | NC | Cadps |
| secretogranin III | −3.0 | NC | Scg3 |
| synaptotagmin 4 | −3.0 | NC | Syt4 |
| exportin 1, CRM1 homolog (yeast) | −3.0 | NC | Xpo1 |
| synaptotagmin-like 4 | −3.0 | NC | Sytl4 |
| glutamate receptor, ionotropic, AMPA2 (alpha 2) | −3.0 | NC | Gria2 |
| synaptosomal-associated protein 25 | −2.8 | NC | Snap25 |
| neuropilin | −2.6 | NC | Nrp |
| secretogranin III | −2.6 | NC | Scg3 |
| synaptosomal-associated protein 25 binding protein | −2.6 | NC | Snap25bp |
| synaptosomal-associated protein 91 | −2.6 | NC | Snap91 |
| synaptotagmin 1 | −2.5 | NC | Syt1 |
| synaptophysin | −2.5 | NC | Syp |
| dynamin 1-like | −2.5 | NC | Dnm1l |
| cytotoxic granule-associated RNA binding protein 1 | −2.5 | NC | Tia1 |
| rabaptin 5 | −2.5 | NC | Rab5ep |
| dynamin | −2.5 | NC | Dnm |
| microtubule-associated protein tau | −2.5 | NC | Mapt |
| syntaxin 4A (placental) | −2.3 | NC | Stx4a |
| secretory granule neuroendocrine protein 1, 7B2 protein | −2.3 | NC | Sgne1 |
| vesicular membrane protein p24 | −2.3 | NC | Vmp |
| coronin, actin binding protein 1A | −2.3 | NC | Coro1a |
| chromogranin A | −2.1 | NC | Chga |
| synaptotagmin-like 4 | −2.1 | NC | Sytl4 |
| coatomer protein complex subunit alpha | −2.1 | NC | Copa |
| dynein, cytoplasmic, light chain 2A | −2.1 | NC | Dncl2a |
| coatomer protein complex, subunit gamma 1 | −2.1 | NC | Copg1 |
| vesicle-associated membrane protein 4 | −2.1 | NC | Vamp4 |
| sec13-like protein | −2.1 | NC | Sec13l |
| calnexin | −2.1 | NC | Canx |
| syntaxin binding protein 3 | −2.1 | NC | Stxbp3 |
| vacuolar protein sorting 16 (yeast) | −2.1 | NC | Vps16 |
| SEC22 vesicle trafficking protein-like 1 (S. cerevisiae) | −2.1 | NC | Sec22l1 |
| coatomer protein complex, subunit beta 2 (beta prime) | −2.1 | NC | Copb2 |
| proteoglycan, secretory granule | −2.0 | NC | Prg |
| syntaxin 6 | −2.0 | NC | Stx6 |
| tubulin, alpha 3 | −2.0 | NC | Tuba3 |
| capping protein alpha 1 | −2.0 | NC | Cappa1 |
| secretory carrier membrane protein 1 | −2.0 | NC | Scamp1 |

*A hyphen before a number indicates a decrease. For example, a fold change of −4.3 indicates a 4.3-fold reduction in gene expression level.
NC means that the change in gene expression level was less than twofold.

These results show that food A repressed genes encoding proteins associated with a chromaffin secretory pathway.

Genes Encoding Products That Regulate Gene Transcription: Functional gene analysis showed that expression levels of genes that regulate transcription were repressed. The list of the affected members of this family is shown in Table 15.

TABLE 15

Repression of Genes That Regulate Gene Transcription in Adrenal Gland

| Gene Name | Food A FOLD change* | Food B FOLD change | Gene Symbol |
|---|---|---|---|
| splicing factor 3b, subunit 1 | −2.5 | NC# | Sf3b1 |
| Trf (TATA binding protein-related factor)-proximal protein homolog (Drosophila) | −2.5 | NC | Trfp |
| RNA binding motif protein 10 | −2.5 | NC | Rbm10 |
| transcription factor 4 | −2.3 | NC | Tcf4 |
| transcription factor 12 | −2.3 | NC | Tcf12 |
| polymerase (DNA directed), beta | −2.3 | NC | Polb |
| CCR4-NOT transcription complex, subunit 2 | −2.3 | NC | Cnot2 |
| cleavage stimulation factor, 3' pre-RNA subunit 2, tau | −2.3 | NC | Cstf2t-pending |
| splicing factor, arginine/serine-rich 1 (ASF/SF2) | −2.3 | NC | Sfrs1 |
| general transcription factor II I | −2.1 | NC | Gtf2i |
| YY1 transcription factor | −2.1 | NC | Yy1 |
| CCAAT/enhancer binding protein alpha (C/EBP), related sequence 1 | −2.1 | NC | Cebpa-rs1 |
| PRP4 pre-mRNA processing factor 4 homolog B (yeast) | −2.1 | NC | Prpf4b |
| splicing factor 3a, subunit 3, 60 kDa | −2.0 | NC | Sf3a3 |
| polymerase (RNA) II (DNA directed) polypeptide H | −2.0 | NC | Polr2h |

*A hyphen before a number indicates a decrease. For example, a fold change of −2.5 indicates a 2.5-fold reduction in gene expression level.
NC means that the change in gene expression level was less than twofold.

These results show that food A repressed genes that encode key enzymes of the transcriptional machinery. This may account for the net decrease in expression of genes in the adrenal gland.

NF-kB Pathway Genes: Functional gene analysis showed that expression levels of genes encoding products that are indicators of active NF-kB pathway or key modulators of its activity were repressed. The list of affected members of this family is shown in Table 16.

TABLE 16

Repression of NF-kB Pathway Genes in Adrenal Gland

| Gene Name | Food A FOLD change* | Food B FOLD change* | Gene symbol |
|---|---|---|---|
| serum amyloid A 3 | −8.0 | −5.3 | Saa3 |
| lymphotoxin B | −4.6 | NC# | Ltb |
| nuclear factor of kappa light polypeptide gene enhancer in B-cells 2, p49/p100 | −2.6 | NC | Nfkb2 |
| nuclear factor of kappa light chain gene enhancer in B-cells inhibitor, alpha | −2.3 | NC | Nfkbia |
| CCAAT/enhancer binding protein alpha (C/EBP), related sequence 1 | −2.1 | NC | Cebpa-rs1 |
| tumor necrosis factor receptor superfamily, member 1a | −2.1 | NC | Tnfrsf1a |
| nuclear factor of kappa light chain gene enhancer in B-cells 1, p105 | −2.0 | NC | Nfkb1 |

*A hyphen before a number indicates a decrease. For example, a fold change of −8.0 indicates a 8.0-fold reduction in gene expression level.
NC means that the change in gene expression level was less than twofold.

These results show that food A repressed expression of genes that encode products that are either indicators of active NF-kB pathway or are key modulators of its activity. Moreover, food B repressed serum amyloid A 3 gene. The coordinated repression of the genes that encode subunits of the transcription factor NF-kB may account for the repression of the genes that cause inflammation and modulate immune responses (see also FIG. 2).

Example 5

The effects of foods A and B on expression of various classes of genes in liver of senescence accelerated mice were determined using the GeneChip assay described above.

Immune Function Related Genes: Functional gene analysis showed that immune function related genes were repressed by foods A and B. The list of the affected members of this family is shown in Table 17.

TABLE 17

Repression of Immune Function-Related Genes in Liver

| Gene Name | Food A FOLD change* | Food B FOLD change* | Gene Symbol |
|---|---|---|---|
| immunoglobulin lambda chain, variable 1 | −78.8 | −78.8 | Igl-V1 |
| histocompatibility 2, class II, locus Mb1 | −52.0 | −6.1 | H2-DMb1 |
| lymphotoxin B | −39.4 | −128.0 | Ltb |
| chemokine (C-C motif) ligand 5 | −34.3 | −27.9 | Ccl5 |
| interferon-induced protein with tetratricopeptide repeats 2 | −29.9 | −10.6 | Ifit2 |
| histocompatibility 2, class II, locus Mb2 | −29.9 | −8.6 | H2-DMb2 |
| orosomucoid 2 | −24.3 | −13.0 | Orm2 |
| immunoglobulin heavy chain 6 (heavy chain of IgM) | −24.3 | −29.9 | Igh-6 |
| immunoglobulin heavy chain 4 (serum IgG1) | −24.3 | −19.7 | Igh-4 |
| CD52 antigen | −22.6 | −32.0 | Cd52 |
| CD24a antigen | −21.1 | −24.3 | Cd24a |
| chemokine (C—X—C motif) receptor 4 | −21.1 | NC# | Cxcr4 |
| interferon regulatory factor 4 | −19.7 | −17.1 | Irf4 |
| neutrophil cytosolic factor 1 | −19.7 | −13.0 | Ncf1 |
| lymphoblastomic leukemia | −18.4 | −64.0 | Lyl1 |
| lymphocyte specific 1 | −18.4 | −48.5 | Lsp1 |
| chemokine (C—X—C motif) ligand 13 | −16.0 | −36.8 | Cxcl13 |
| serum amyloid A 2 | −16.0 | −6.1 | Saa2 |
| immunoglobulin kappa chain variable 8 (V8) | −16.0 | −13.0 | Igk-V8 |
| CD79B antigen | −14.9 | −14.9 | Cd79b |

*A hyphen before a number indicates a decrease. For example, a fold change of −78.8 indicates a 78.8-fold reduction in gene expression level.
NC means that the change in gene expression level was less than twofold.

These results show that foods A and B repressed genes related to immune function. Coordinated repressions of genes that encode heavy and light (variable, antigen binding) peptide chains of immunoglobulins suggest that foods A and B may modulate the humoral "arm" of the immune system and suggesting the importance of each in regulating the functions of the lymphocytes. Since these transcripts are normally associated with lymphocytes and the transcripts were detected in the liver, the data suggest that foods A and B may target the lymphatic system, at least that of the liver. The repressive effects of foods A and B on the lymphocyte functions are further supported by the repression of the mRNAs for CD 79, CD 52 and CD24. As shown in Table 17, food B appears to be more potent at suppressing the activities of the lymphocytes.

Foods A and B have anti-inflammatory profiles in the adrenal gland and the liver. The repression of these genes may be partially accounted for by the repression of the genes that encode subunits of the pro-inflammatory transcription factors, nuclear factor kappa B (NF-kB), mitogen activated protein (MAP) kinases, and stimulator and activator of transcription (STAT).

Genes Encoding Glycolytic Enzymes And Mitochondrial Oxidative Pathway Proteins: Functional gene analysis showed that genes encoding glycolytic enzymes and mitochondrial oxidative pathway proteins are repressed by foods A and B. The list of affected members of this family is shown in Table 18.

TABLE 18

Repression of Genes That Encode Glycolytic Enzymes and Mitochondrial Oxidative Pathway Proteins in Liver

| Gene Name | Food A FOLD change* | Food B FOLD change* | Gene symbol |
|---|---|---|---|
| pyruvate dehydrogenase kinase, isoenzyme 3 | −9.2 | −13.9 | Pdk3 |
| pyruvate kinase, muscle | −6.5 | −5.7 | Pkm2 |
| phosphofructokinase, platelet | −4.6 | −5.7 | Pfkp |
| adenylosuccinate lyase | −4.3 | −3.7 | Adsl |
| aldolase 1, A isoform | −3.7 | −3.2 | Aldo1 |
| hexokinase 1 | −3.2 | −2.3 | Hk1 |
| glyceraldehyde-3-phosphate dehydrogenase | −3.2 | −2.1 | Gapd |
| phosphofructokinase, liver, B-type | −3.2 | NC# | Pfkl |
| glucose phosphate isomerase 1 | −3.0 | −2.3 | Gpi1 |
| 6-phosphogluconolactonase | −3.0 | −2.1 | Pgls |
| transaldolase 1 | −3.0 | −2.1 | Taldo1 |
| Transketolase | −3.0 | NC | Tkt |
| 2,3-bisphosphoglycerate mutase | −2.8 | −2.6 | Bpgm |
| ATP citrate lyase | −2.6 | −2.5 | Acly |
| ATPase, H+ transporting, V0 subunit B | −2.6 | −1.9 | Atp6v0b |
| ATPase, H+ transporting, V0 subunit D isoform 1 | −2.6 | −1.9 | Atp6v0d1 |
| cytochrome c oxidase subunit VIIa polypeptide 2-like | −2.6 | −1.9 | Cox7a2l |
| ATPase, H+ transporting, V1 subunit A, isoform 1 | −2.6 | NC | Atp6v1a1 |
| NADH dehydrogenase (ubiquinone) 1 alpha subcomplex, 3 | −2.6 | NC | Ndufa3 |
| enolase 1, alpha non-neuron | −2.5 | −1.7 | Eno1 |

*A hyphen before a number indicates a decrease. For example, a fold change of −9.2 indicates a 9.2-fold reduction in gene expression level.
NC means that the change in gene expression level was less than twofold.

These results show that foods A and B repress expression of the genes that encode rate controlling enzymes in glucose and pyruvate metabolism. The effects of foods A and B on the genes that encode the enzymes of the intermediary metabolism indicated their distinct and tissue-specific effects. These actions mimic those of caloric restriction.

Genes Encoding Ribosomal Proteins: Functional gene analysis showed that genes encoding ribosomal proteins were repressed by foods A and B. The list of the affected members of this family is shown in Table 19.

TABLE 19

Repression of Genes That Encode Ribosomal Proteins in Liver

| Gene Name | Food A FOLD change* | Food B FOLD change* | Gene Symbol |
|---|---|---|---|
| mitochondrial ribosomal protein L54 | −4.3 | NC# | Mrpl54 |
| ribosomal protein S11 | −4.0 | −3.2 | Rps11 |
| ribosomal protein S19 | −4.0 | −2.3 | Rps19 |
| mitochondrial ribosomal protein L44 | −3.7 | −1.9 | Mrpl44 |
| ribosomal protein L13a | −3.5 | −3.2 | Rpl13a |
| ribosomal protein S8 | −3.5 | −3.0 | Rps8 |
| ribosomal protein S12 | −3.5 | −2.8 | Rps12 |
| ribosomal protein S26 | −3.5 | −2.6 | Rps26 |
| ribosomal protein L27a | −3.5 | −2.5 | Rpl27a |
| ribosomal protein L8 | −3.2 | −2.8 | Rpl8 |
| ribosomal protein S23 | −3.2 | −2.8 | Rps23 |
| ribosomal protein L37 | −3.2 | −2.6 | Rpl37 |
| ribosomal protein L13 | −3.2 | −2.5 | Rpl13 |
| ribosomal protein S3 | −3.2 | −2.5 | Rps3 |

*A hyphen before a number indicates a decrease. For example, a fold change of −4.3 indicates a 4.3-fold reduction in gene expression level.
NC means that the change in gene expression level was less than twofold.

These results show that foods A and B repress the activities of the genes that encode ribosomal proteins. A possible consequence of these effects of the two foods would be inhibition of protein synthesis and may be related to the inhibition of glucose and pyruvate metabolism suggested in Table 17.

Genes Encoding Heat Shock Proteins: Functional gene analysis showed that genes encoding heat shock proteins were repressed. The list of affected members of this family is shown in Table 20.

TABLE 20

Repression of Genes Encoding Heat Shock Proteins in Liver

| Gene Name | Food A FOLD change* | Food B FOLD change* | Gene symbol |
|---|---|---|---|
| heat shock protein | −5.7 | −2.6 | Hspl05 |
| heat shock protein 1, alpha | −5.3 | −3.2 | Hspca |
| DnaJ (Hsp40) homolog, subfamily C, member 7 | −4.3 | −2.8 | Dnajc7 |
| heat shock protein 1, beta | −3.2 | −2.3 | Hspcb |
| heat shock protein 4 | −2.8 | NC# | Hspa4 |
| heat shock protein 8 | −2.8 | NC | Hspa8 |
| DnaJ (Hsp40) homolog, subfamily C, member 2 | −2.6 | NC | Dnajc2 |
| heat shock 70 kD protein 5 (glucose-regulated protein) | −2.6 | NC | Hspa5 |

*A hyphen before a number indicates a decrease. For example, a fold change of −5.7 indicates a 5.7-fold reduction in gene expression level.
NC means that the change in gene expression level was less than twofold.

These results show that in liver, foods A and B repress genes that encode heat shock proteins. These genes are transcriptionally regulated and are induced in response to cellular stress such as oxidant-stress. As discussed earlier, antioxidant effects of foods A and B is suggested by decrease in the activities of the genes encoding heat shock proteins, chaperonins, and protein disulfide isomerases in both liver and adrenal gland (see also Table 9). The results are notable in lacking effects on the expression of classical antioxidant genes such as those for SODs and catalases.

Genes Encoding DNA Repair Enzymes: Functional gene analysis showed that genes encoding DNA repair enzymes were repressed. The list of affected members of this family is shown in Table 21.

TABLE 21

Repression of Genes That Are Induced by DNA Damage

| Gene Name | Food A FOLD change* | Food B FOLD change* | Gene symbol |
|---|---|---|---|
| neuroblastoma ras oncogene | −3.5 | −2.6 | Nras |
| retinoblastoma binding protein 7 | −3.2 | −2.5 | Rbbp7 |
| retinoblastoma binding protein 4 | −3.2 | −2.3 | Rbbp4 |
| RAD21 homolog (*S. pombe*) | −2.8 | −2.1 | Rad21 |
| retinoblastoma 1 | −2.8 | NC# | Rb1 |

*A hyphen before a number indicates a decrease. For example, a fold change of −3.5 indicates a 3.5-fold reduction in gene expression level.
NC means that the change in gene expression level was less than twofold.

These results show that in liver, foods A and B repress genes that encode DNA repair enzymes. These genes are transcriptionally regulated and are induced in response to cellular stress, such as oxidant-stress, or DNA damage.

Example 6

The effects of foods A and B on expression of various classes of genes in cerebral cortex of SAM were determined using the GeneChip assay described above. Results from those assays are presented in Tables 22 (food A) and 23 (food B).

TABLE 22

Effect of Food A on the Expression of Genes in the Cerebral Cortex

| Gene Name | Food A FOLD change* |
|---|---|
| Ia-associated invariant chain | −3.0 |
| ring finger protein 4 | −2.8 |
| T-cell specific GTPase | −2.8 |
| adaptor-related protein complex 2, beta 1 subunit | −2.6 |
| disrupted in bipolar disorder 1 homolog (human) | −2.6 |
| proprotein convertase subtilisin/kexin type 5 | −2.5 |
| homer homolog 1 (*Drosophila*) | −2.5 |
| transgene insert site 737, insertional mutation, polycystic kidney disease | −2.5 |
| homeo box A4 | −2.5 |
| RIKEN cDNA D930018N21 gene | −2.3 |
| paternally expressed 10 | −2.3 |
| glucose phosphate isomerase 1 | −2.3 |
| immunoglobulin kappa chain variable 8 (V8) | −2.1 |
| valosin containing protein | −2.1 |
| tubulin, beta 2 | −2.1 |
| A kinase (PRKA) anchor protein 8 | −2.1 |
| HLA-B associated transcript 2 | −2.1 |
| guanylate nucleotide binding protein 2 | −2.1 |
| B-cell receptor-associated protein 37 | −2.1 |
| histocompatibility 2, Q region locus 7 | −2.1 |
| polymerase (DNA directed), delta 1, catalytic subunit | −2.1 |
| major urinary protein 1 | −2.1 |
| RAS-related C3 botulinum substrate 2 | −2.0 |
| erythrocyte protein band 7.2 | −2.0 |
| BTB (POZ) domain containing 3 | −2.0 |
| major urinary protein 3 | −2.0 |
| somatostatin receptor 2 | −2.0 |
| runt related transcription factor 2 | −2.0 |
| placenta-specific 8 | −2.0 |
| protease, serine, 25 | −2.0 |
| integrin alpha 3 | −2.0 |
| hypothetical protein MGC41229 | −2.0 |
| DiGeorge syndrome critical region gene 6 | −2.0 |
| Vimentin | −2.0 |
| aminolevulinic acid synthase 2, erythroid | −2.0 |
| SRY-box containing gene 18 | −2.0 |
| calcium/calmodulin-dependent protein kinase II alpha | −2.0 |
| formin-like | −2.0 |
| formin-like | −2.0 |
| hemoglobin, beta adult major chain | −2.0 |
| syntaxin 3 | 2.0 |
| forkhead box C1 | 2.0 |
| distal-less homeobox 1 | 2.1 |
| transmembrane 4 superfamily member 8 | 2.1 |
| interferon-induced protein with tetratricopeptide repeats 2 | 2.1 |
| sulfotransferase family 1A, phenol-preferring, member 1 | 2.3 |
| pre B-cell leukemia transcription factor 3 | 2.5 |
| eomesodermin homolog (*Xenopus laevis*) | 7.0 |

*A hyphen before a number indicates a decrease. For example, a fold change of −3.5 indicates a 3.5-fold reduction in gene expression level.
NC means that the change in gene expression level was less than twofold.

TABLE 23

Effect of Food B on the Expression of Genes in the Cerebral Cortex

| Gene Name | Food B FOLD change* |
|---|---|
| myelocytomatosis oncogene | −3.7 |
| gap junction membrane channel protein beta 6 | −3.6 |
| group specific component | −3.4 |
| cytochrome P450, family 3, subfamily a, polypeptide 11 | −3.4 |
| zinc finger protein 146 | −3.3 |
| major urinary protein 1 | −3 |
| DNA methyltransferase 3A | −3 |
| tubulin, beta 5 | −2.9 |
| HLA-B associated transcript 2 | −2.7 |
| interferon-inducible GTPase | −2.4 |
| adaptor-related protein complex 2, beta 1 subunit | −2.2 |
| major urinary protein 1 | −2.2 |
| RIKEN cDNA 2610016K11 gene | −2.1 |

TABLE 23-continued

Effect of Food B on the Expression of Genes in the Cerebral Cortex

| Gene Name | Food B FOLD change* |
|---|---|
| acidic (leucine-rich) nuclear phosphoprotein 32 family, member A | 2 |
| parotid secretory protein | 2.1 |
| cadherin 15 | 2.2 |
| ESTs | 2.7 |
| RIKEN cDNA 1110061O04 gene | 4.5 |
| Socius | 6.3 |

*A hyphen before a number indicates a decrease. For example, a fold change of −3.5 indicates a 3.5-fold reduction in gene expression level.
NC means that the change in gene expression level was less than twofold.

As discussed above, FIG. 4 shows the functional classification and the relative distribution of the differentially expressed genes in the cerebral cortex of mice fed food A. A similar distribution of differentially expressed genes was detected in the cerebral cortex of mice fed food B.

Figure 5:
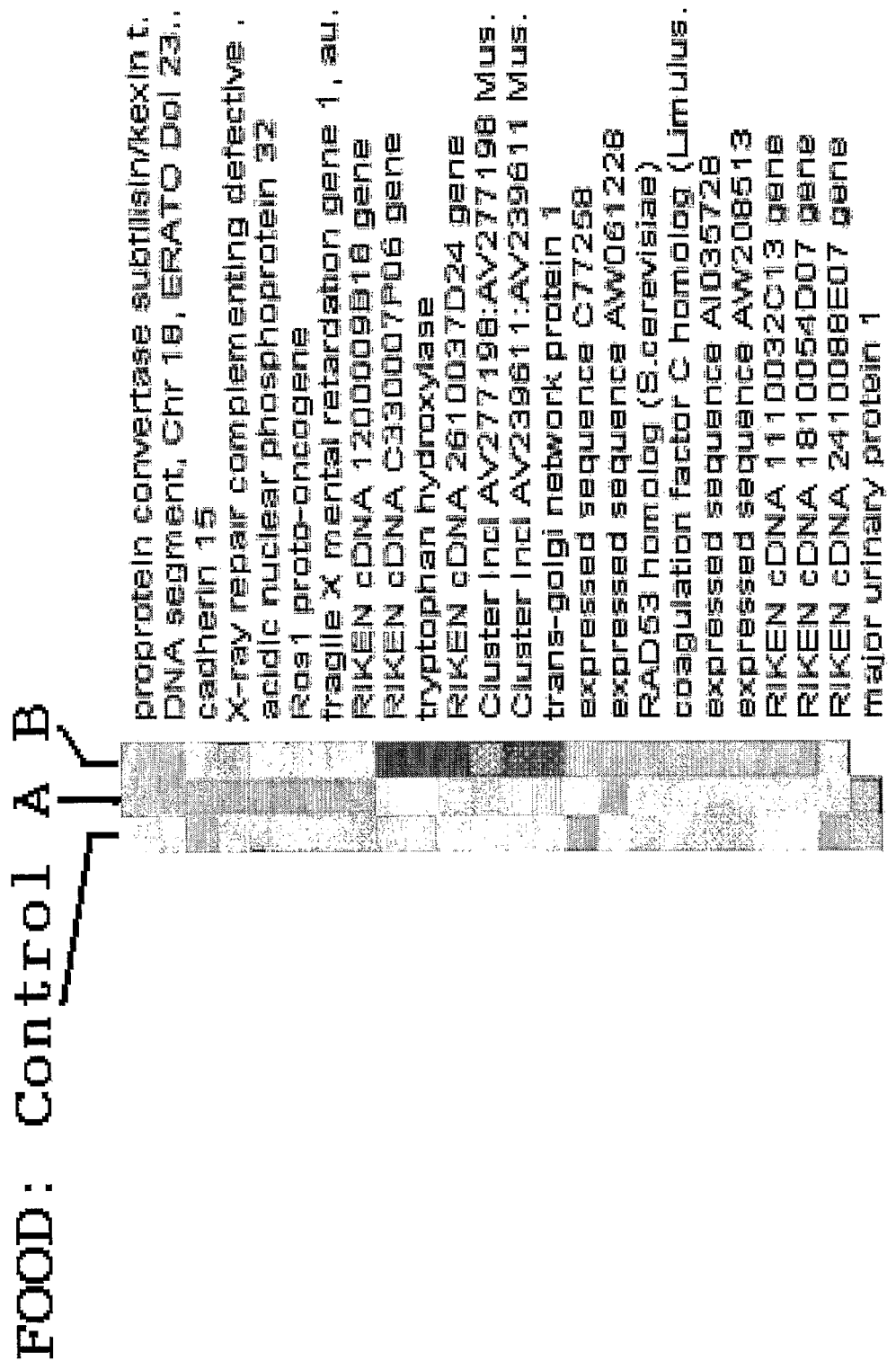
FIG. 5 shows the differential effects of control food and foods A and B on gene expression by "hierarchal cluster analysis" of mRNA expression profiles.

FIG. 5 illustrates the differential effects of control food, food A, and food B by "hierarchical cluster analysis" of mRNA expression profiles obtained by GeneChip analysis described above. In FIG. 5, genes that show low relative expression have "light" or "soft" colors and those that show high relative expression have bright colors. The range of changes is 2 standard deviation units.

The total numbers of cerebral cortex genes affected by the foods A and B was much lower than that detected in liver and adrenal gland and may suggest greater "protection" of this organ by direct effects of the dietary components. In addition to the fewer numbers of affected genes, the range of the effect on the expression of the cerebral genes is also narrow. For example, in the liver, the effects on the expression of genes range from −130-fold to +3-fold and in the adrenal from −10-fold to +45 fold, whereas in the cerebral cortex the range of change in the expression range from −3 fold to +7 fold.

As shown in FIG. 4, genes related to immune function and transcription factors form the largest clusters of affected genes. The data is particularly noteworthy with respect to the lack of effects on genes that encode heat shock and cell cycle proteins. However, a number of genes that regulate synaptic function such as "Homer 1" are repressed by foods A and B to a similar extent. Homer 1 regulates the targeting of specific subunits of glutamate receptors to the synaptic membrane and regulates the actions of calcium ions. Similarly, both foods A and B also repress the expression of the gene for calcium/calmodulin-dependent protein kinase, further supporting the suggestion that foods A and B modulate the calcium-dependent signal transduction pathways. Also, the mRNA for dual specificity phosphatase, an enzyme important in regulating the signal transduction pathways by protein kinases, is induced ~20 fold by food B.

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method of treating oxidative stress in a canine in need thereof, the method comprising:
   treating the oxidative stress in the canine by administering to the canine in need thereof a pet food composition comprising:
      two or more antioxidants selected from a first group consisting of vitamin E, vitamin C, lipoic acid, and L-carnitine;
      one or more antioxidants selected from a second group consisting of astaxanthin, rice bran, algae, curcumin, marine oil, and yeast; and
      one or more antioxidants selected from a third group consisting of coenzyme Q10, lutein, lycopene, polyphenol(s), tocotrienol(s), selenium, and green tea;
      wherein a total amount of the two or more antioxidants in the first group, the one or more antioxidants in the second group, and the one or more antioxidants in the third group in the composition are sufficient to treat the oxidative stress in the canine in need thereof, and
   measuring a decrease in a ratio of reduced glutathione (GSH) to oxidized glutathione (GSSG) in a sample from a canine in need thereof relative to a control value for the ratio of GSH to GSSG in a sample from a normal canine or population of canines, and/or relative to a previous individual baseline value from the canine,
   measuring a down-regulation or an up-regulation of one or more genes selected from the group consisting of: cytochrome P450 genes, apolipoprotein genes, genes regulating hemodynamic properties, heat shock protein genes, genes regulating DNA damage, genes regulating cell cycle pathways, pro-inflammatory genes, chromaffin secretory genes, genes regulating gene transcription, NK-kB genes, genes encoding glycolytic or mitochondrial oxidative enzymes, genes encoding ribosomal protein to indicate treatment,
   wherein the ratio of GSH to GSSG is an indicator of oxidative stress,
   wherein the one or more genes includes cytochrome P450 genes,
   wherein measuring the down-regulation or the up-regulation of the one of more genes comprises measuring an up-regulation of the cytochrome P450 genes, and
   wherein the cytochrome P450 genes are selected from the group consisting of: P450, family 2, subfamily b, polypeptide 10 (Cyp2b10); P450, family 2, subfamily c, polypeptide 70 (Cyp2c70); P450, family 2, subfamily c, polypeptide 37 (Cyp2c37); P450, family 2, subfamily a, polypeptide 12 (Cyp2a12); P450, family 2, subfamily c, polypeptide 40 (Cyp2c40); P450, family 3, subfamily a, polypeptide 11 (Cyp3a11); P450, family 3, subfamily a, polypeptide 13 (Cyp3a15); P450, family 3, subfamily a, polypeptide 16 (Cyp3a16); P450, family 3, subfamily a, polypeptide 25 (Cyp3a25); P450, family 2, subfamily a, polypeptide 4 (Cyp2a4); P450, family 4, subfamily a, polypeptide 10 (Cyp4a10), and combinations thereof.

2. The method of claim 1, wherein the canine is at least 7 years old.

3. The method of claim 1, wherein the two or more antioxidants in the first group, the one or more antioxidants in the second group, and the one or more antioxidants in the third group are also sufficient to treat a deterioration of cognitive function in the canine, wherein the cognitive function is at least one of memory loss, memory impairment, learning impairment, disorientation, and reduction in mental alertness.

4. The method of claim 1, wherein the composition comprises the rice bran.

5. The method of claim 1, wherein the composition comprises the algae.

6. The method of claim 1, wherein the composition comprises the curcumin.

7. A method of treating oxidative stress in a canine in need thereof, the method comprising:
   treating the oxidative stress in the canine by administering to the canine in need thereof a pet food composition comprising: broccoli, rice bran, marine oil, glutamine dipeptide, methionine, selenium, algae, L-threonine, lutein, lycopene, astaxanthin, beta-carotene, curcumin, and one or more antioxidants selected from the group consisting of vitamin E, vitamin C;
   measuring an up-regulation of cytochrome P450 genes to indicate treatment; and
   measuring an up-regulation of apolipoprotein genes to indicate treatment.

8. The method of claim 1, wherein the sample is a blood sample.

9. The method of claim 1, wherein the sample is a tissue sample.

10. The method of claim 9, wherein the tissue sample is skeletal muscle.

11. The method of claim 9, wherein the tissue sample comprises one or more of the following: liver tissue, kidney tissue, heart tissue, cerebral cortex, and skeletal muscle.

12. The method of claim 7, wherein the sample is a blood sample.

13. The method of claim 7, wherein the sample is a tissue sample.

14. The method of claim 13, wherein the tissue sample is skeletal muscle.

15. The method of claim 13, wherein the tissue sample comprises one or more of the following: liver tissue, kidney tissue, heart tissue, cerebral cortex, and skeletal muscle.

16. The method of claim 1, wherein the one or more genes further includes the apolipoprotein genes, and wherein measuring the down-regulation or the up-regulation of the one or more genes comprises measuring an up-regulation of the apolipoprotein genes.

17. The method of claim 16, wherein the apolipoprotein genes are selected from the group consisting of: apolipoprotein C-II (Apoc2), apolipoprotein A-I (Apoa1), apolipoprotein A-II (Apoa2), apolipoprotein A-V (Apoa5), apolipoprotein H (Apoh), and combinations thereof.

18. The method of claim 7, wherein the apolipoprotein genes are selected from the group consisting of: apolipoprotein C-II (Apoc2), apolipoprotein A-I (Apoa1), apolipoprotein A-II (Apoa2), apolipoprotein A-V (Apoa5), apolipoprotein H (Apoh), and combinations thereof.

19. The method of claim 18, wherein the cytochrome P450 genes are selected from the group consisting of: P450, family 2, subfamily b, polypeptide 10 (Cyp2b10); P450, family 2, subfamily c, polypeptide 70 (Cyp2c70); P450, family 2, subfamily c, polypeptide 37 (Cyp2c37); P450, family 2, subfamily a, polypeptide 12 (Cyp2a12); P450, family 2, subfamily c, polypeptide 40 (Cyp2c40); P450, family 3, subfamily a, polypeptide 11 (Cyp3a11); P450, family 3, subfamily a, polypeptide 13 (Cyp3a15); P450, family 3, subfamily a, polypeptide 16 (Cyp3a16); P450, family 3, subfamily a, polypeptide 25 (Cyp3a25); P450, family 2, subfamily a, polypeptide 4 (Cyp2a4); P450, family 4, subfamily a, polypeptide 10 (Cyp4a10), and combinations thereof.

* * * * *

UNITED STATES PATENT AND TRADEMARK OFFICE
CERTIFICATE OF CORRECTION

Page 1 of 1

PATENT NO. : 11,077,165 B2
APPLICATION NO. : 11/718963
DATED : August 3, 2021
INVENTOR(S) : Steven Curtis Zicker et al.

It is certified that error appears in the above-identified patent and that said Letters Patent is hereby corrected as shown below:

On the Title Page

Item (60), "Related U.S. Application Date", delete "60/626,162" and insert -- 60/626,126 --, therefor.

On Page 2, Item (56), Column 2, Line 2, delete "44675-4682" and insert -- 44675-44682 --, therefor.

In the Specification

In Column 1, Line 11, delete "TEE" and insert -- THE --, therefor.

In Column 20, Line 22, delete "Pro-inflamatory" and insert -- Pro-inflammatory --, therefor.

In the Claims

In Column 28, Line 24, in Claim 1, after "oxidized", delete "glutathione" and insert
-- glutathionine --, therefor.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*